US010942186B2

United States Patent
Figeys et al.

(10) Patent No.: US 10,942,186 B2
(45) Date of Patent: Mar. 9, 2021

(54) METHOD FOR PROFILING PROTEIN METHYLATION

(71) Applicant: UNIVERSITY OF OTTAWA, Ottawa (CA)

(72) Inventors: Daniel Figeys, Ottawa (CA); Zhibin Ning, Ottawa (CA); Anna Sylvia Mierzwa, Windsor (CA)

(73) Assignee: UNIVERSITY OF OTTAWA, Ottawa (CA)

( * ) Notice: Subject to any disclaimer, the term of this patent is extended or adjusted under 35 U.S.C. 154(b) by 296 days.

(21) Appl. No.: 15/738,861

(22) PCT Filed: Jun. 23, 2016

(86) PCT No.: PCT/CA2016/050736
§ 371 (c)(1),
(2) Date: Dec. 21, 2017

(87) PCT Pub. No.: WO2016/205943
PCT Pub. Date: Dec. 29, 2016

(65) Prior Publication Data
US 2018/0188262 A1    Jul. 5, 2018

Related U.S. Application Data

(60) Provisional application No. 62/183,212, filed on Jun. 23, 2015.

(51) Int. Cl.
| | |
|---|---|
| *G01N 33/68* | (2006.01) |
| *C40B 20/08* | (2006.01) |
| *G01N 30/18* | (2006.01) |
| *G01N 30/96* | (2006.01) |
| *G01N 30/14* | (2006.01) |
| G01N 30/88 | (2006.01) |
| C12N 9/10 | (2006.01) |

(52) U.S. Cl.
CPC ......... *G01N 33/6812* (2013.01); *C40B 20/08* (2013.01); *G01N 30/14* (2013.01); *G01N 30/96* (2013.01); *C12N 9/1007* (2013.01); *G01N 2030/8831* (2013.01); *G01N 2440/12* (2013.01)

(58) Field of Classification Search
CPC .... G01N 33/6812; G01N 30/96; G01N 30/14; G01N 2440/12; G01N 2030/8831; C40B 20/08; C12N 9/1007
See application file for complete search history.

(56) References Cited

PUBLICATIONS

Wu—A Chemical Proteomics Approach for Global Analysis of Lysine Monomethylone Profiling—2015 (Year: 2015).*

(Continued)

*Primary Examiner* — Lyle Alexander
*Assistant Examiner* — Jean Caraballo-Leon
(74) *Attorney, Agent, or Firm* — BCF LLP

(57) ABSTRACT

There is provided a method for identifying protein methylation on arginine and lysine residues. The method comprises obtaining a set of peptides; blocking un-methylated arginine and lysine residues and the free N-terminal amine of peptides in the set of peptides, so that un-methylated peptides are neutralized and only methylated peptides are positively charged at neutral or basic pH; isolating the methylated peptides based on charge; and performing mass spectrometry (MS) analysis on the isolated methylated peptides to detect methylated lysine and arginine residues. Methods provided herein can be used for large scale, high throughput profiling of protein methylation in a cell or tissue.

17 Claims, 45 Drawing Sheets
Specification includes a Sequence Listing.

(56) References Cited

PUBLICATIONS

Roth—Fluorescence Reaction for Amino Acids—Analytical Chemistry—1970 (Year: 1971).*

Bremang—Mass spec based identification and characterization of lysine and arginine methylation in the human proteome—Molecular Biosystems—2013 (Year: 2013).*

ThermoFisher—Fluoraldehyde o—Phthaldialdehyde Reagent Solution OPA—https://www.thermofisher.com/order/catalog/product/26025#/26025 (Year: 2011).*

GE LifeSciences (HiTrap ™ Capto ™ IEX Selection Kit, Product 28934388, 2008 as per the "First Published" date on the last page of the instructions for the kit) (Year: 2008).*

Foettinger, Alexandra et al., "Derivatisation of arginine residues with malondialdehyde for the analysis of peptides and protein digests by LC-ESI-MS/MS", Journal of Mass Spectrometry, 2006, vol. 41, pp. 623-632.

Benson, James R. et al., "o-Phthalaldehyde: Fluorogenic Detection of Primary Amines in the Picomole Range. Comparison with Fluorescamine and Ninhydrin", Proc. Nat. Acad. Sci. USA, 1975, vol. 72(2), pp. 619-622.

Pahlich, Steffen et al., "Protein arginine methylation : Cellular functions and methods of analysis", Biochimica Et Biophysica Acta, 2006, vol. 1764, pp. 1890-1903.

International Search Report and Written Opinion of the International Searching Authority for PCT/CA2016/050736, dated Aug. 18, 2016.

\* cited by examiner

```
..A....K........          .......RGG..G..
.A.....K.......           .......RG.....G
.V.....K.......           ......GR......R
```

Lysine Mono-methylation     Arginine Di-methylation

A:

B:

C:

A

B

A

B

A

B

Monoisotopic mass of neutral peptide Mr(calc): 1500.7249
Fixed modifications: Carbamidomethyl (C) (apply to specified residues or termini only)
Variable modifications:
N-term : OPA (N-term)
K7 : Methyl-Mono (K)
R11 : MDA (R)
Ions Score: 66  Expect: 0.00036
Matches : 15/108 fragment ions using 24 most intense peaks

| # | b | b++ | b* | Seq. | y | y++ | y* | # |
|---|---|---|---|---|---|---|---|---|
| 1 | 246.0761 | 123.5417 | | E | | | | 11 |
| 2 | 359.1601 | 180.0837 | | I | 1256.6634 | 628.8353 | 1239.6368 | 10 |
| 3 | 430.1973 | 215.6023 | | A | 1143.5793 | 572.2933 | 1126.5528 | 9 |
| 4 | 558.2558 | 279.6316 | 541.2293 | Q | 1072.5422 | 536.7747 | 1055.5156 | 8 |
| 5 | 673.2828 | 337.1450 | 656.2562 | D | 944.4836 | 472.7454 | 927.4571 | 7 |
| 6 | 820.3512 | 410.6792 | 803.3246 | F | 829.4567 | 415.2320 | 812.4301 | 6 |
| 7 | 962.4618 | 481.7345 | 945.4353 | K | 682.3883 | 341.6978 | 665.3617 | 5 |
| 8 | 1063.5095 | 532.2584 | 1046.4829 | T | 540.2776 | 270.6425 | 523.2511 | 4 |
| 9 | 1178.5364 | 589.7719 | 1161.5099 | D | 439.2300 | 220.1186 | 422.2034 | 3 |
| 10 | 1291.6205 | 646.3139 | 1274.5939 | L | 324.2030 | 162.6051 | 307.1765 | 2 |
| 11 | | | | R | 211.1190 | 106.0631 | 194.0924 | 1 |

Monoisotopic mass of neutral peptide Mr(calc): 1500.7249
Fixed modifications: Carbamidomethyl (C) (apply to specified residues or termini only)
Variable modifications:
N-term : OPA (N-term)
K7    : Methyl-Mono (KR)
R11   : MDA (R)
Ions Score: 55  Expect: 9.2e-005
Matches : 19/108 fragment ions using 37 most intense peaks

| # | b | b⁺⁺ | b* | Seq | y | y⁺⁺ | y* | # |
|---|---|---|---|---|---|---|---|---|
| 1 | 246.0761 | 123.5417 | | E | | | | 11 |
| 2 | 359.1601 | 180.0837 | | I | *1256.6634* | 628.8353 | 1239.6368 | 10 |
| 3 | 430.1973 | 215.6023 | | A | *1143.5793* | 572.2933 | 1126.5528 | 9 |
| 4 | 558.2558 | 279.6316 | 541.2293 | Q | *1072.5422* | 536.7747 | 1055.5156 | 8 |
| 5 | 673.2828 | 337.1450 | 656.2562 | D | *944.4836* | 472.7454 | 927.4571 | 7 |
| 6 | 820.3512 | 410.6792 | 803.3246 | F | *829.4567* | 415.2320 | 812.4301 | 6 |
| 7 | 962.4618 | 481.7345 | 945.4353 | K | *682.3883* | 341.6978 | 665.3617 | 5 |
| 8 | 1063.5095 | 532.2584 | 1046.4829 | T | *540.2776* | 270.6425 | 523.2511 | 4 |
| 9 | 1178.5364 | 589.7719 | 1161.5099 | D | 439.2300 | 220.1186 | 422.2034 | 3 |
| 10 | 1291.6205 | 646.3139 | 1274.5939 | L | *324.2030* | 162.6051 | 307.1765 | 2 |
| 11 | | | | R | *211.1190* | 106.0631 | 194.0924 | 1 |

Monoisotopic mass of neutral peptide Mr(calc): 1528.7562
Fixed modifications: Carbamidomethyl (C) (apply to specified residues or termini only)
Variable modifications:
N-term : OPA (N-term)
K7     : Methyl-Tri (K)
R11    : MDA (R)
Ions Score: 44  Expect: 0.066
Matches : 10/108 fragment ions using 12 most intense peaks

| #  | b         | b++      | b*        | Seq. | y         | y++      | y*        | #  |
|----|-----------|----------|-----------|------|-----------|----------|-----------|----|
| 1  | 246.0761  | 123.5417 |           | E    |           |          |           | 11 |
| 2  | 359.1601  | 180.0837 |           | I    | 1284.6947 | 642.8510 | 1267.6681 | 10 |
| 3  | 430.1973  | 215.6023 |           | A    | 1171.6106 | 586.3089 | 1154.5841 | 9  |
| 4  | 558.2558  | 279.6316 | 541.2293  | Q    | 1100.5735 | 550.7904 | 1083.5469 | 8  |
| 5  | 673.2828  | 337.1450 | 656.2562  | D    | 972.5149  | 486.7611 | 955.4884  | 7  |
| 6  | 820.3512  | 410.6792 | 803.3246  | F    | 857.4880  | 429.2476 | 840.4614  | 6  |
| 7  | 990.4931  | 495.7502 | 973.4666  | K    | 710.4196  | 355.7134 | 693.3930  | 5  |
| 8  | 1091.5408 | 546.2740 | 1074.5142 | T    | 540.2776  | 270.6425 | 523.2511  | 4  |
| 9  | 1206.5677 | 603.7875 | 1189.5412 | D    | 439.2300  | 220.1186 | 422.2034  | 3  |
| 10 | 1319.6518 | 660.3295 | 1302.6252 | L    | 324.2030  | 162.6051 | 307.1765  | 2  |
| 11 |           |          |           | R    | 211.1190  | 106.0631 | 194.0924  | 1  |

Monoisotopic mass of neutral peptide Mr(calc): 1528.7562
Fixed modifications: Carbamidomethyl (C) (apply to specified residues or termini only)
Variable modifications:
N-term : OPA (N-term)
K7   : Methyl-Tri (K)
R11  : MDA (R)
Ions Score: 64  Expect: 0.00015
Matches : 12/108 fragment ions using 13 most intense peaks

| # | b | b++ | b* | Seq | y | y++ | y* | # |
|---|---|---|---|---|---|---|---|---|
| 1 | 246.0761 | 123.5417 | | E | | | | 11 |
| 2 | 359.1601 | 180.0837 | | I | *1284.6947* | 642.8510 | 1267.6681 | 10 |
| 3 | 430.1973 | 215.6023 | | A | 1171.6106 | 586.3089 | 1154.5841 | 9 |
| 4 | 558.2558 | 279.6316 | 541.2293 | Q | *1100.5735* | 550.7904 | 1083.5469 | 8 |
| 5 | 673.2828 | 337.1450 | 656.2562 | D | *972.5149* | 486.7611 | 955.4884 | 7 |
| 6 | 820.3512 | 410.6792 | 803.3246 | F | *857.4880* | 429.2476 | 840.4614 | 6 |
| 7 | 990.4931 | 495.7502 | 973.4666 | K | *710.4196* | 355.7134 | 693.3930 | 5 |
| 8 | 1091.5408 | 546.2740 | 1074.5142 | T | 540.2776 | 270.6425 | 523.2511 | 4 |
| 9 | 1206.5677 | 603.7875 | 1189.5412 | D | 439.2300 | 220.1186 | 422.2034 | 3 |
| 10 | 1319.6518 | 660.3295 | 1302.6252 | L | *324.2030* | 162.6051 | 307.1765 | 2 |
| 11 | | | | R | *211.1190* | 106.0631 | 194.0924 | 1 |

Monoisotopic mass of neutral peptide Mr(calc): 1529.7701
Fixed modifications: Carbamidomethyl (C) (apply to specified residues or termini only)
Variable modifications:
N-term : OPA (N-term)
K3    : Methyl-Di (K)
R11   : MDA (R)
Ions Score: 66  Expect: 0.00054
Matches : 10/120 fragment ions using 13 most intense peaks

| #  | b         | b++      | b*        | Seq. | y         | y++      | y*        | #  |
|----|-----------|----------|-----------|------|-----------|----------|-----------|----|
| 1  | 245.0921  | 123.0497 | 228.0655  | Q    |           |          |           | 11 |
| 2  | 408.1554  | 204.5813 | 391.1288  | Y    | 1286.6926 | 643.8499 | 1269.6660 | 10 |
| 3  | 564.2817  | 282.6445 | 547.2551  | K    | 1123.6292 | 562.3183 | 1106.6027 | 9  |
| 4  | 621.3031  | 311.1552 | 604.2766  | G    | 967.5030  | 484.2551 | 950.4764  | 8  |
| 5  | 734.3872  | 367.6972 | 717.3606  | I    | 910.4815  | 455.7444 | 893.4550  | 7  |
| 6  | 847.4713  | 424.2393 | 830.4447  | I    | 797.3974  | 399.2024 | 780.3709  | 6  |
| 7  | 962.4982  | 481.7527 | 945.4716  | D    | 684.3134  | 342.6603 | 667.2868  | 5  |
| 8  | 1122.5288 | 561.7681 | 1105.5023 | C    | 569.2864  | 285.1469 | 552.2599  | 4  |
| 9  | 1221.5973 | 611.3023 | 1204.5707 | V    | 409.2558  | 205.1315 | 392.2292  | 3  |
| 10 | 1320.6657 | 660.8365 | 1303.6391 | V    | 310.1874  | 155.5973 | 293.1608  | 2  |
| 11 |           |          |           | R    | 211.1190  | 106.0631 | 194.0924  | 1  |

Monoisotopic mass of neutral peptide Mr(calc): 1543.7857
Fixed modifications: Carbamidomethyl (C) (apply to specified residues or termini only)
Variable modifications:
N-term : OPA (N-term)
K3     : Methyl-Tri (K)
R11    : MDA (R)
Ions Score: 53  Expect: 0.012
Matches : 17/120 fragment ions using 28 most intense peaks

| #  | b         | b++      | b*        | Seq. | y         | y++      | y*        | #  |
|----|-----------|----------|-----------|------|-----------|----------|-----------|----|
| 1  | 245.0921  | 123.0497 | 228.0655  | Q    |           |          |           | 11 |
| 2  | 408.1554  | 204.5813 | 391.1288  | Y    | 1300.7082 | 650.8577 | 1283.6817 | 10 |
| 3  | 578.2973  | 289.6523 | 561.2708  | K    | 1137.6449 | 569.3261 | 1120.6183 | 9  |
| 4  | 635.3188  | 318.1630 | 618.2922  | G    | 967.5030  | 484.2551 | 950.4764  | 8  |
| 5  | 748.4028  | 374.7051 | 731.3763  | I    | 910.4815  | 455.7444 | 893.4550  | 7  |
| 6  | 861.4869  | 431.2471 | 844.4604  | I    | 797.3974  | 399.2024 | 780.3709  | 6  |
| 7  | 976.5138  | 488.7606 | 959.4873  | D    | 684.3134  | 342.6603 | 667.2868  | 5  |
| 8  | 1136.5445 | 568.7759 | 1119.5179 | C    | 569.2864  | 285.1469 | 552.2599  | 4  |
| 9  | 1235.6129 | 618.3101 | 1218.5864 | V    | 409.2558  | 205.1315 | 392.2292  | 3  |
| 10 | 1334.6813 | 667.8443 | 1317.6548 | V    | 310.1874  | 155.5973 | 293.1608  | 2  |
| 11 |           |          |           | R    | 211.1190  | 106.0631 | 194.0924  | 1  |

Monoisotopic mass of neutral peptide Mr(calc): 1543.7857
Fixed modifications: Carbamidomethyl (C) (apply to specified residues or termini only)
Variable modifications:
N-term : OPA (N-term)
K3  : Methyl-Tri (K)
R11  : MDA (R)
Ions Score: 48  Expect: 0.0021
Matches : 11/120 fragment ions using 13 most intense peaks

| # | b | b++ | b* | Seq. | y | y++ | y* | # |
|---|---|---|---|---|---|---|---|---|
| 1 | 245.0921 | 123.0497 | 228.0655 | Q |  |  |  | 11 |
| 2 | 408.1554 | 204.5813 | 391.1288 | Y | 1300.7082 | 650.8577 | 1283.6817 | 10 |
| 3 | 578.2973 | 289.6523 | 561.2708 | K | 1137.6449 | 569.3261 | 1120.6183 | 9 |
| 4 | 635.3188 | 318.1630 | 618.2922 | G | 967.5030 | 484.2551 | 950.4764 | 8 |
| 5 | *748.4028* | 374.7051 | 731.3763 | I | 910.4815 | 455.7444 | 893.4550 | 7 |
| 6 | *861.4869* | 431.2471 | 844.4604 | I | 797.3974 | 399.2024 | 780.3709 | 6 |
| 7 | *976.5138* | 488.7606 | 959.4873 | D | 684.3134 | 342.6603 | 667.2868 | 5 |
| 8 | *1136.5445* | 568.7759 | 1119.5179 | C | 569.2864 | 285.1469 | 552.2599 | 4 |
| 9 | *1235.6129* | 618.3101 | 1218.5864 | V | 409.2558 | 205.1315 | 392.2292 | 3 |
| 10 | *1334.6813* | 667.8443 | 1317.6548 | V | 310.1874 | 155.5973 | 293.1608 | 2 |
| 11 |  |  |  | R | 211.1190 | 106.0631 | 194.0924 | 1 |

Monoisotopic mass of neutral peptide Mr(calc): 1617.7133
Fixed modifications: Carbamidomethyl (C) (apply to specified residues or termini only)
Variable modifications:
N-term : OPA (N-term)
K11   : Methyl-Di (K)
R12   : MDA (R)
Ions Score: 60 Expect: 0.00043
Matches : 11/96 fragment ions using 13 most intense peaks

| #  | b         | b++      | b*       | Seq. | y         | y++      | y*        | #  |
|----|-----------|----------|----------|------|-----------|----------|-----------|----|
| 1  | 248.0740  | 124.5406 |          | M    |           |          |           | 12 |
| 2  | 363.1009  | 182.0541 |          | D    | 1371.6539 | 686.3306 | 1354.6274 | 11 |
| 3  | 450.1329  | 225.5701 |          | S    | 1256.6270 | 628.8171 | 1239.6004 | 10 |
| 4  | 551.1806  | 276.0940 |          | T    | 1169.5950 | 585.3011 | 1152.5684 | 9  |
| 5  | 680.2232  | 340.6152 |          | E    | 1068.5473 | 534.7773 | 1051.5207 | 8  |
| 6  | 777.2760  | 389.1416 |          | P    | 939.5047  | 470.2560 | 922.4781  | 7  |
| 7  | 874.3287  | 437.6680 |          | P    | 842.4519  | 421.7296 | 825.4254  | 6  |
| 8  | 1037.3921 | 519.1997 |          | Y    | 745.3992  | 373.2032 | 728.3726  | 5  |
| 9  | 1124.4241 | 562.7157 |          | S    | 582.3358  | 291.6715 | 565.3093  | 4  |
| 10 | 1252.4827 | 626.7450 | 1235.4561| Q    | 495.3038  | 248.1555 | 478.2772  | 3  |
| 11 | 1408.6089 | 704.8081 | 1391.5824| K    | 367.2452  | 184.1262 | 350.2187  | 2  |
| 12 |           |          |          | R    | 211.1190  | 106.0631 | 194.0924  | 1  |

Monoisotopic mass of neutral peptide Mr(calc): 1617.7133
Fixed modifications: Carbamidomethyl (C) (apply to specified residues or termini only)
Variable modifications:
N-term : OPA (N-term)
K11    : Methyl-Di (KR)
R12    : MDA (R)
Ions Score: 52  Expect: 1.3e-005
Matches : 10/96 fragment ions using 14 most intense peaks

| # | b | b++ | b* | Seq. | y | y++ | y* | # |
|---|---|---|---|---|---|---|---|---|
| 1 | 248.0740 | 124.5406 | | M | | | | 12 |
| 2 | *363.1009* | 182.0541 | | D | *1371.6539* | 686.3306 | 1354.6274 | 11 |
| 3 | 450.1329 | 225.5701 | | S | *1256.6270* | 628.8171 | 1239.6004 | 10 |
| 4 | 551.1806 | 276.0940 | | T | *1169.5950* | 585.3011 | 1152.5684 | 9 |
| 5 | 680.2232 | 340.6152 | | E | *1068.5473* | 534.7773 | 1051.5207 | 8 |
| 6 | 777.2760 | 389.1416 | | P | *939.5047* | 470.2560 | 922.4781 | 7 |
| 7 | 874.3287 | 437.6680 | | P | *842.4519* | 421.7296 | 825.4254 | 6 |
| 8 | 1037.3921 | 519.1997 | | Y | 745.3992 | 373.2032 | 728.3726 | 5 |
| 9 | 1124.4241 | 562.7157 | | S | *582.3358* | 291.6715 | 565.3093 | 4 |
| 10 | 1252.4827 | 626.7450 | 1235.4561 | Q | 495.3038 | 248.1555 | 478.2772 | 3 |
| 11 | 1408.6089 | 704.8081 | 1391.5824 | K | 367.2452 | 184.1262 | 350.2187 | 2 |
| 12 | | | | R | 211.1190 | 106.0631 | 194.0924 | 1 |

A

B

SEQUENCE LISTING

```
<160> NUMBER OF SEQ ID NOS: 5

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide

<400> SEQUENCE: 1

Glu Ile Ala Gln Asp Phe Lys Thr Asp Leu Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Glu Ile Ala Gln Asp Phe Lys Thr Asp Leu Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic peptide

<400> SEQUENCE: 3

Gln Tyr Lys Gly Ile Ile Asp Cys Val Val Arg
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide

<400> SEQUENCE: 4

Gln Tyr Lys Gly Ile Ile Asp Cys Val Val Arg
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide

<400> SEQUENCE: 5
```

-continued

```
Met Asp Ser Thr Glu Pro Pro Tyr Ser Gln Lys Arg
1           5                   10
```

METHOD FOR PROFILING PROTEIN METHYLATION

RELATED APPLICATIONS

This application claims priority to U.S. Provisional Application No. 62/183,212 filed Jun. 23, 2015, the entire contents of which are hereby incorporated by reference.

FIELD OF THE INVENTION

The present disclosure broadly relates to methods for large scale, high throughput profiling of protein methylation.

BACKGROUND OF THE INVENTION

Protein post-translational modifications (PTMs) play important roles in the regulation of molecular interactions and biological functions. Lysine and arginine methylation on histones has been extensively studied for its role in epigenetics and regulation of gene expression. It has been estimated that 0.7-1% of the arginine residues in proteins are methylated (Bulau, P. et al., Biotechniques 40: 305-310 (2006)). However, fewer protein methylation events have been discovered to date than expected, primarily because of the difficulty in developing methods to enrich methylated proteins (Guo, A. et al., Mol Cell Proteomics 13: 372-387 (2014)), which is compounded by their low stoichiometry (Mann, M. & Jensen, O. N., Nature biotechnology 21: 255-261 (2003)).

Current strategies for detecting protein methylation rely mainly on prediction, fractionation, use of pan-specific antibodies, and methylation binding domains. Such approaches are usually designed using peptides with known consensus sequences, and may therefore have sequence targeting bias.

Recently, an approach based on chemically modifying mono-methylated lysine by propionylation and antibody enrichment was reported (Wu, Z. et al., Mol. Cell Proteomics 14: 329-339, 2015). However this approach was limited to mono-methylated lysine and relies on antibodies. RK-methylation-specific antibodies and binding domains recognize peptides with known consensus sequences and therefore usually exhibit sequence recognition bias (Uhlmann, T. et al., Molecular & cellular proteomics: MCP 11: 1489-1499, 2012; Boisvert, F. M. et al., Molecular & cellular proteomics: MCP 2: 1319-1330, 2003). Although antibody-based strategies have thus far provided the highest numbers of putative methylated peptides, the routine characterization of protein methylation is limited by the quality and availability of antibodies.

There is a need for improved methods for protein methylome analysis and to identify protein methylation on lysine and arginine residues.

SUMMARY OF THE INVENTION

It is an object of the present invention to ameliorate at least some of the deficiencies present in the prior art. Embodiments of the present technology have been developed based on the inventors' appreciation that there is a need for improved methods to identify and/or profile protein methylation in a cell or tissue.

The present disclosure relates to a novel chemical strategy for identifying methylation on lysine and arginine residues in which tryptic peptides are subjected to chemical derivatization to eliminate the charges on un-modified lysine or arginine residues and peptide N-terminals. Peptides containing methylated lysine or arginine residues remain positively charged and are then enriched based on charge (for example, using strong cation exchange), followed by mass spectrometry (MS) analysis.

In brief, in some embodiments there is provided a novel charge-suppressing strategy to probe RK-methylated peptides, involving the derivatization of the side-chains of un-methylated RK residues. Methylated RK side-chains are unaffected by the reactions, retain their charges and can therefore be separated from un-methylated peptides. In an embodiment, a protein extract is first digested into peptides using trypsin. The tryptic peptide mixture is then reacted with malondialdehyde (MDA) and ortho-phthalaldehyde (OPA) sequentially to suppress the positive charges of side chains' primary amine groups of un-methylated RK residues and free N-terminal amines of peptides. Without wishing to be limited by theory, it is believed that these two reactions block most of the positive charge-carrying functional groups in the digested peptides, mainly leaving behind methylated peptides with a positive charge at neutral to basic pH. The methylated peptides can then be readily enriched by charge-based separation techniques, such as strong cation-exchange chromatography, whereas un-methylated peptides co-enriched by non-specific binding would be hard to ionize due to a lack of charges and are therefore less likely to be identified by mass spectrometry (MS). The MDA-OPA reaction generally shows little or no preference for specific motifs around RK residues. Histidine is the only positively charged amino acid residue that may not be blocked by this approach, and therefore histidine-containing peptides may also be enriched.

In some embodiments, therefore, there are provided methods for protein methylome analysis that are antibody-free, e.g., methods capturing protein methylation on RK residues using chemical reactions to eliminate the charges on un-modified RK residues and peptide N-termini, such that peptides containing methylated RK residues remain positively charged and are then enriched by strong cation exchange chromatography, followed by high-resolution mass spectrometry identification, without relying on specific antibodies.

Embodiments of the methods described herein may provide one or more of the following advantages: simple and/or inexpensive, i.e., cost-effective; antibody-free, i.e., do not rely on specific antibodies to perform charge-based methylated peptide enrichment and identification by MS; non-sequence-biased, i.e., no sequence targeting bias; and/or suitable for use for large-scale methylome profiling and/or methyltransferase/demethylase discovery.

In a first broad aspect, there is provided a method for identifying methylation on arginine and lysine residues in a set of peptides, the method comprising: i) obtaining the set of peptides; ii) chemically derivatizing peptides in the set of peptides, so that un-methylated peptides are neutralized and only methylated peptides are positively charged at neutral or basic pH; iii) isolating methylated peptides based on charge; and iv) performing mass spectrometry (MS) analysis on the isolated methylated peptides to detect methylated lysine and arginine residues.

In some embodiments, step (ii) comprises blocking un-methylated arginine and lysine residues and the free N-terminal amine of peptides in the set of peptides.

In some embodiments, step (ii) comprises conversion of the guanidine group on un-methylated arginine residues to a 2-pyrimidine residue, for example by reaction with malondialdehyde (MDA) or an acetal or derivative thereof, e.g., by reaction with 1,1,3,3-tetraisopropoxypropane (TiPP). In embodiments, step (ii) further comprises blocking the epsilon primary amine on un-methylated lysine residues and blocking the free primary amine on the peptide N-terminals, for example by reaction with ortho-phthalaldehyde (OPA) or a derivative thereof.

In certain embodiments, step (ii) comprises sequential reaction with MDA or TiPP and OPA, e.g., reaction with MDA or TiPP, followed by reaction with OPA.

In some embodiments, reaction with MDA is carried out in a strongly acidic aqueous environment, e.g., in about 6-12 M hydrochloric acid (HCl).

In some embodiments, an acetal precursor form of MDA or a derivative of MDA is used in step (ii) to block un-methylated arginine residues. In some embodiments, a derivative of OPA is used in step (ii) to block un-methylated lysine residues.

In some embodiments, reaction with 1,1,3,3-tetraisopropoxypropane (TiPP) is carried out, leading to in situ production of MDA. In some embodiments, reaction with TiPP is carried out in an acidic aqueous environment, e.g., in the presence of HCl. In further embodiments, TiPP and HCl are pre-incubated with an excess of acetic acid. Without wishing to be limited by theory, it is believed that such pre-incubation with an excess of acetic acid may suppress protein esterification, which generally occurs under strong acidic conditions, and thus reduce the false-positive identification of mono-, di- or trimethylation on adjacent targeted amino acids (e.g., arginine, lysine and histidine).

In some embodiments, step (iii) comprises ion exchange fractionation e.g., strong cation exchange (SCX) such as solid phase extraction (SPE).

In some embodiments, the set of peptides comprises tyrptic peptides obtained by digesting a set of proteins with trypsin. For example, the set of proteins may be present in, or isolated from, a cellular extract or lysate.

In some embodiments, methods provided herein are free of sequence targeting bias. In other words, un-methylated arginine and lysine residues are blocked in step (ii) regardless of the peptide sequence.

In another broad aspect, there is provided a method for large scale profiling of protein methylation in a cell or tissue, the method comprising: i) digesting proteins from the cell or tissue with trypsin, to provide a set of tryptic peptides; ii) blocking un-methylated arginine and lysine residues and the free N-terminal amine of peptides in the tryptic set of peptides, so that un-methylated peptides are neutralized and only methylated peptides are positively charged at neutral or basic pH; iii) isolating methylated peptides based on charge; and iv) performing mass spectrometry (MS) analysis on the isolated methylated peptides to detect methylated lysine and arginine residues.

In some embodiments, methods provided herein are capable of application in a high throughput assay for detecting protein methylation.

In another embodiment, there is provided a method comprising: i) digesting proteins from a cell or tissue with trypsin, to provide a set of tryptic peptides; ii) chemically derivatizing peptides in the tryptic set of peptides, wherein the chemical derivatizing acts to neutralize un-methylated peptides, so that only methylated peptides are positively charged at neutral or basic pH; iii) isolating methylated peptides based on charge; and iv) performing mass spectrometry (MS) analysis on the isolated methylated peptides to detect methylated lysine and arginine residues. In some embodiments, the chemical derivatizing in step (ii) comprises blocking un-methylated arginine and lysine residues and the free N-terminal amine of peptides in the tryptic set of peptides, for example by treatment with MDA or TiPP and OPA.

In a further broad aspect, there are provided kits for identifying protein methylation on arginine and lysine residues in a set of peptides and/or for profiling protein methylation in a cell or tissue, comprising one or more reagent for chemical derivatization of a peptide and instructions for use thereof. For example, instructions for carrying out the chemical derivatization of the peptide(s) may be included. In some embodiments, instructions for carrying out the methods described herein are provided. In some embodiments, the one or more reagent comprises MDA, TiPP, and/or OPA. A kit may also include additional reagents, solvents, buffers, etc., required for carrying out the methods described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a better understanding of the invention and to show more clearly how it may be carried into effect, reference will now be made by way of example to the accompanying drawings, which illustrate aspects and features according to embodiments of the present invention, and in which.

DETAILED DESCRIPTION

Figure 1:
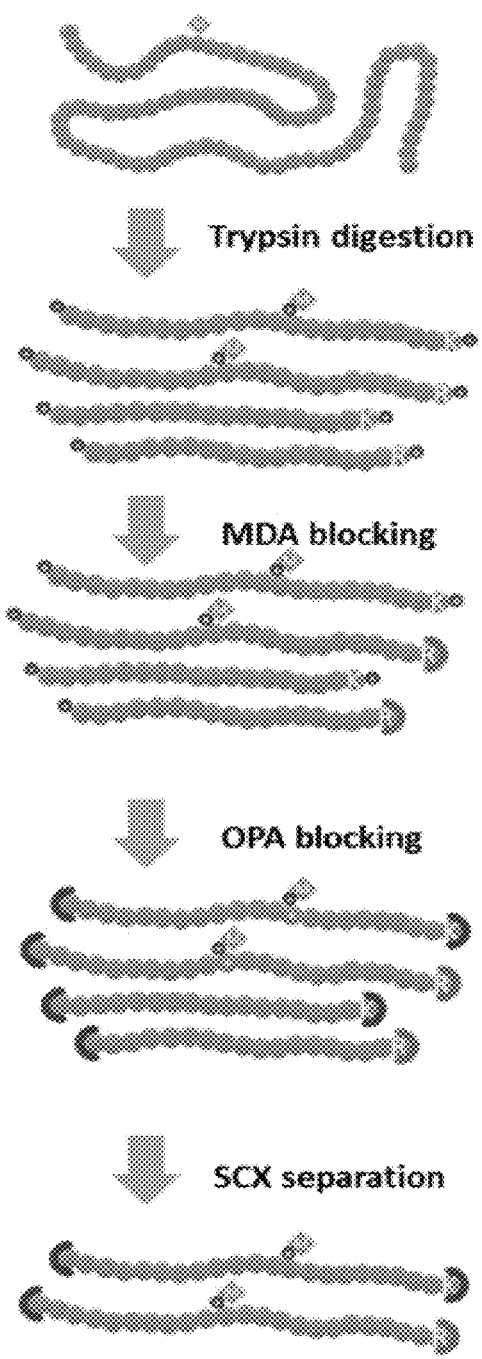
FIG. 1 shows the rationale and workflow of an embodiment of methods of the invention. A: Schematic diagram of an embodiment of the method. Proteins are digested by trypsin to expose lysine and arginine residues at the peptide C-termini. Tryptic peptides are then subjected to MDA and OPA reactions sequentially to block the un-methylated arginine side chains (grey caps), then un-methylated lysine side chains and the N-termini of all peptides (dark blue caps). Only the methylated peptides (with orange diamonds representing methylation modification) will carry positive charges (indicated by a red dot with white cross) under neutral and basic conditions, and can therefore be enriched or purified using charge-based methods, such as ion exchange fractionation. B: Schematic diagram showing overall identified methylation site profile, for mono-, di-, tri-methylation on lysine and mono-, di-methylation on arginine. A detailed summary of methylation site profile for lysine, arginine, and histidine is also shown in FIG. 18. C: Histogram showing the enrichment effect for different pH elution from SCX presented as the ratio of methylated peptide to all the peptide identified, from 3% to 9%, in one embodiment. Negative control experiment is shown in (G). D: Histogram of Mascot score distribution of peptides with methylation sites identified. Red dotted line indicates the density curve, in one embodiment. E: Graph showing the estimated FDR introduced by the MDA/OPA modification, in one embodiment. The effect of adding MDA-OPA as variable modification in increasing the FDR is negligible as the background FDR. F: Spectra validation of peptide EIAQDFK(mono-meth)TDLR from large scale identification (left) and synthesized peptide analysis (right), in one embodiment. Matched fragmentation ions are presented as bold red. G: Negative control experiment for methylation enrichment. Distribution of the peptide identification from MDA-OPA is shown in (C). Results shown in (C) and (G) indicate that the methylated peptides account for a negligible portion (around 0.1%) of all the peptides identified, compared with the significant enrichment (up to 10%) by the MDA-OPA strategy.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "chemical derivatization of a peptide" is used to indicate blocking un-methylated arginine and lysine residues as well as the free N-terminal amine of a peptide chemically, i.e., by chemical reaction with one or more reagent that eliminates positive charges on un-methylated arginine and lysine residues and on the free N-terminal amine. The terms "derivatization" and "derivatizing" are used interchangeably herein.

Although OPA is used in the examples described herein, it should be understood that any reagent that can react with un-methylated lysine residues to eliminate their charge can be used in methods of the invention. It is expressly intended that the method is not limited to reagents (e.g., OPA, OPA derivatives) described herein, and that any suitable reagent that can block the charges on un-methylated lysines and/or the free primary amine on the peptide N-terminal can be used in methods of the invention.

Similarly, the reagent used to react with un-methylated arginine residues to eliminate their charge is not particularly limited. It should be understood that any suitable reagent that can block the charges on un-methylated arginines, e.g., by converting the guanidine group on un-methylated arginine residues to a 2-pyrimidine residue, is intended to be encompassed. With regard to MDA, it is noted that MDA is often supplied in acetal form (e.g., as tetramethoxy- or tetraethoxy-propane) due to its reactivity and instability. MDA acetals can be used to generate free MDA in situ under acidic aqueous conditions. Suitable MDA acetals or other derivatives or precursors may be used in methods of the invention.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Example 1. Negative Selection Strategy for Neutralizing Un-Methylated Peptides

We developed a negative selection strategy by neutralizing un-methylated peptides allowing the enrichment of methylated peptides based on their remaining charges. A schematic diagram showing the workflow of the method is shown in FIG. 1A. Briefly, the proteome was first digested into peptides using trypsin. Then, two subsequent chemical reactions with malondialdehyde (MDA) and ortho-phthalaldehyde (OPA) were used to block the un-methylated arginine and lysine residues, as well as the free N-terminal amine of peptides, to eliminate their positive charges. These two reactions blocked most of the charge-carrying functional groups (N-terminal, lysine, and arginine residues) in digested peptides, leaving mainly methylated peptides carrying charges at neutral or basic pH (FIG. 3).

The methylated peptides were then readily enriched by strong ion exchange (e.g., strong cation exchanger, or SCX). Moreover, any background un-methylated peptides eluted from the SCX had poor ionization and fragmentation efficiency during MS analysis due to the lack of charges, and therefore were less likely to be ionized and identified. It is noted that the MDA-OPA reactions do not generally have motif preferences around lysine/arginine residues in contrast to enrichment of modified peptides using antibody based approaches which have often shown strong motif preferences due to the sequence used for the antibody development. We identified over 1400 methylation events from HEK293 cell lysate using this approach, the largest methylation dataset ever reported.

In the first step of the method, arginine residues within the tryptic peptides were derivatized by MDA (FIG. 3), e.g., using MDA in hydrochloric acid (HCl). Conversion of arginine's guanidine group to a 2-pyrimidine residue using MDA in a strongly acidic aqueous environment has been reported by King (King, T. P., Biochemistry 5: 3454-3459 (1966)) and optimized for proteomics by Foettinger et al. (Foettinger, A. et al., J. Mass. Spectrom. 41: 623-632 (2006)). Derivatization of arginine residues was very stable and led to a reduction in the pKa of arginine of from about 12.5 to about 3.6 (Foettinger, A. et al., J. Mass. Spectrom. 41: 623-632 (2006)). More importantly, mono- and di-methylated arginine residues cannot react with MDA to form a pyrimidine ring due to steric hindrance and therefore retain their charges.

Figure 3:
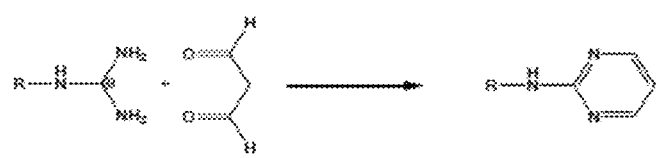
FIG. 3 shows the mechanisms involved in the MDA and OPA chemical reactions. A: The guanidine group of arginine is blocked by malondialdehyde (MDA) in solution to form the 2-pyrimidinyl ring, with greatly reduced basicity and proton affinity. B: Ortho-phthalaldehyde (OPA) reacts with primary amine in the presence of sulfydryl. The primary product is fluorescent at 340 nm. It will gradually decompose into an intermediate then into a non-fluorescent stable product. C: 1,1,3,3-Tetramethoxypropane (TMP) is converted into 1,1,3,3-tretra-isopropoxypropane (TiPP) as the source of malondialdehyde (MDA) in situ to reduce ester formation during the reaction with arginine. D, E: An overview of the MDA (D) and OPA (E) chemical reactions is shown. It is noted that the OPA reaction with the peptide N-terminus occurs via the same mechanism as that for lysine side chains.
Figure 3:
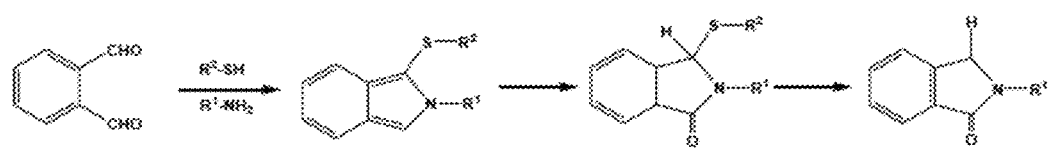
Figure 3:
Figure 3D:
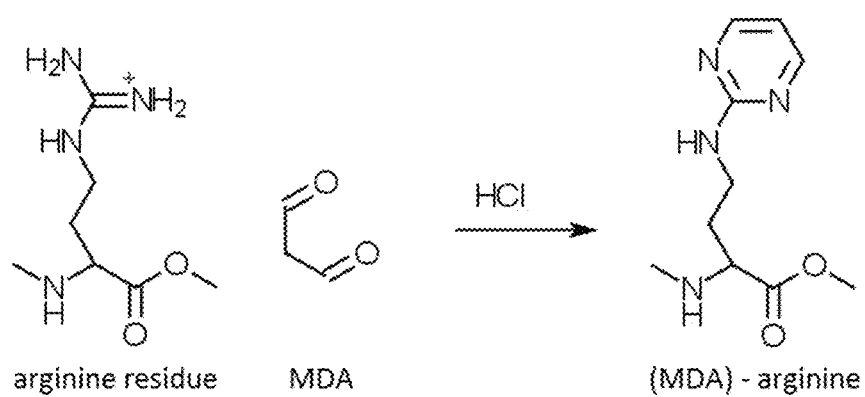
Figure 3E:
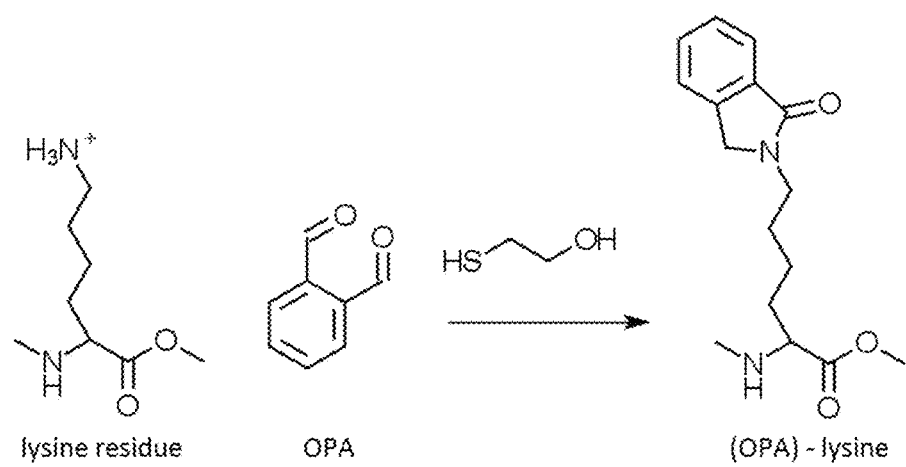
Figure 16:
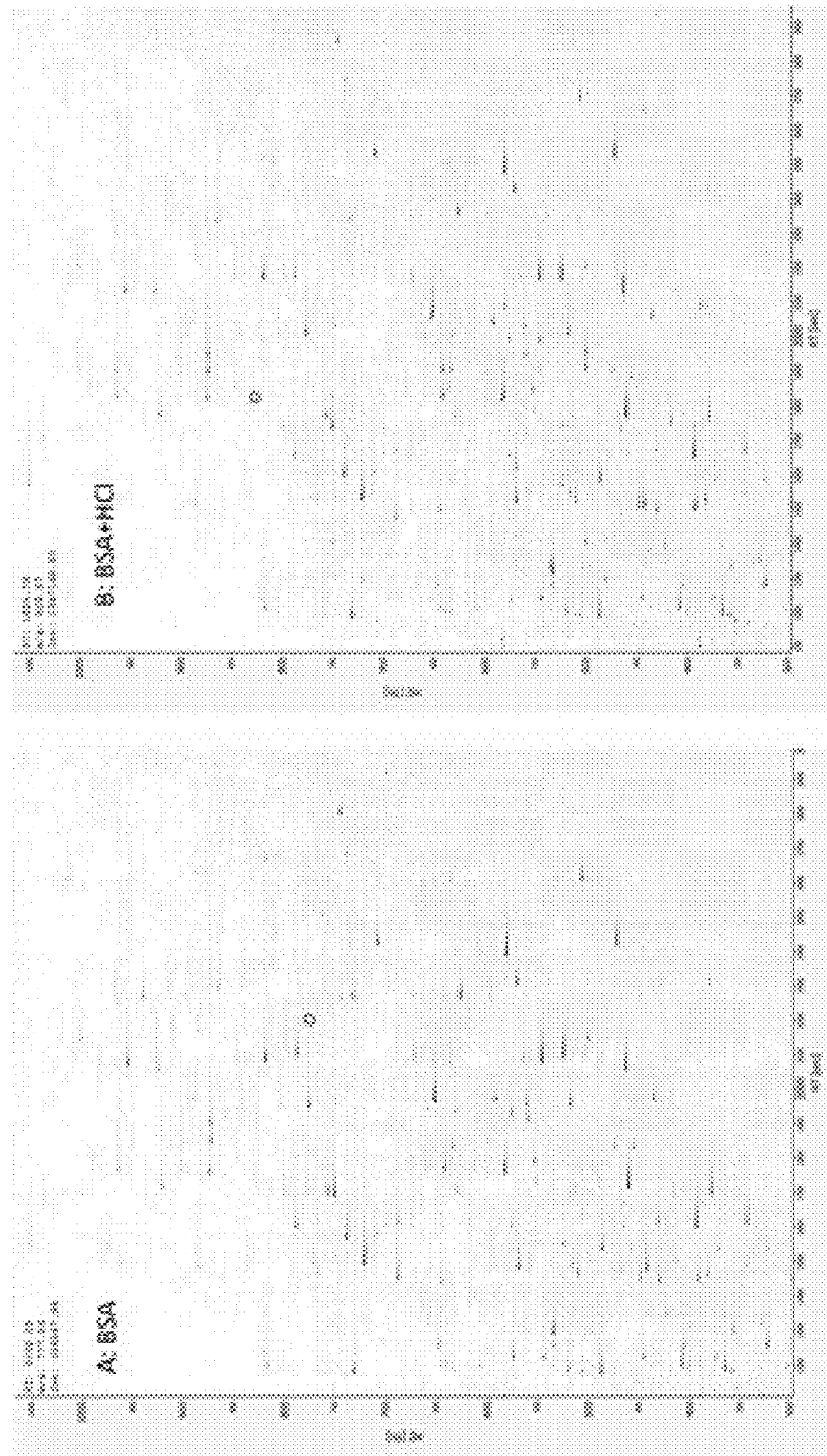
FIG. 16 shows virtual 2D plots of BSA tryptic peptide analysis under different conditions, including BSA only as negative control (A), BSA+HCl (B), BSA+HCl+Methanol (C), BSA+HCl+Methanol+Acetic acid (D), BSA+HCl+Ethanol (E), and BSA+HCl+Ethanol+Acetic acid (F). X axis is the retention time, y axis is the m/z. HCl incubation does not bring obvious degradation or modification judging from the 2D map showing that acetic acid can efficiently reverse the esterification generated by adding methanol or ethanol. Thus acetic acid can efficiently suppress protein esterification.
Figure 16:
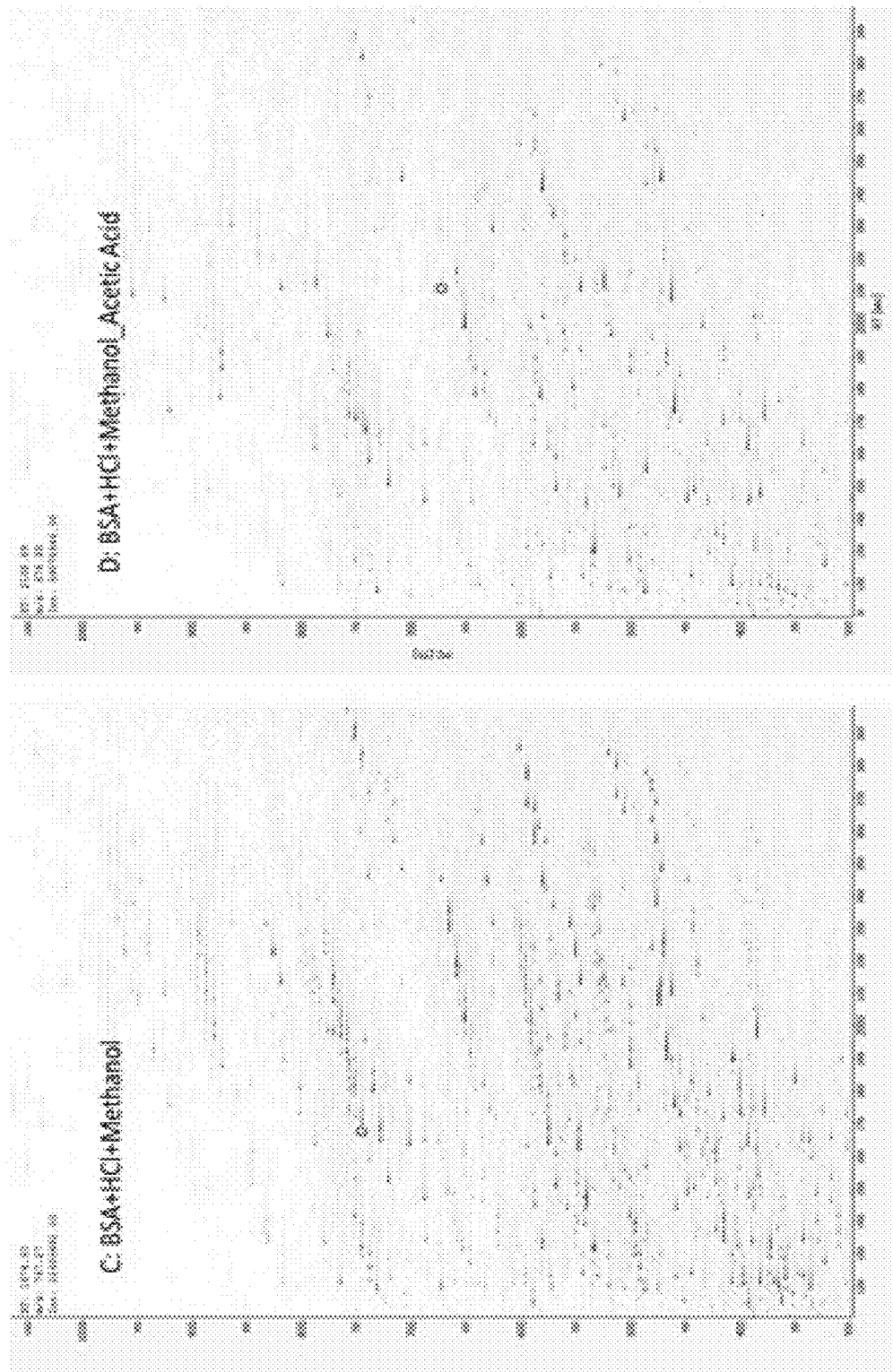
Figure 16:
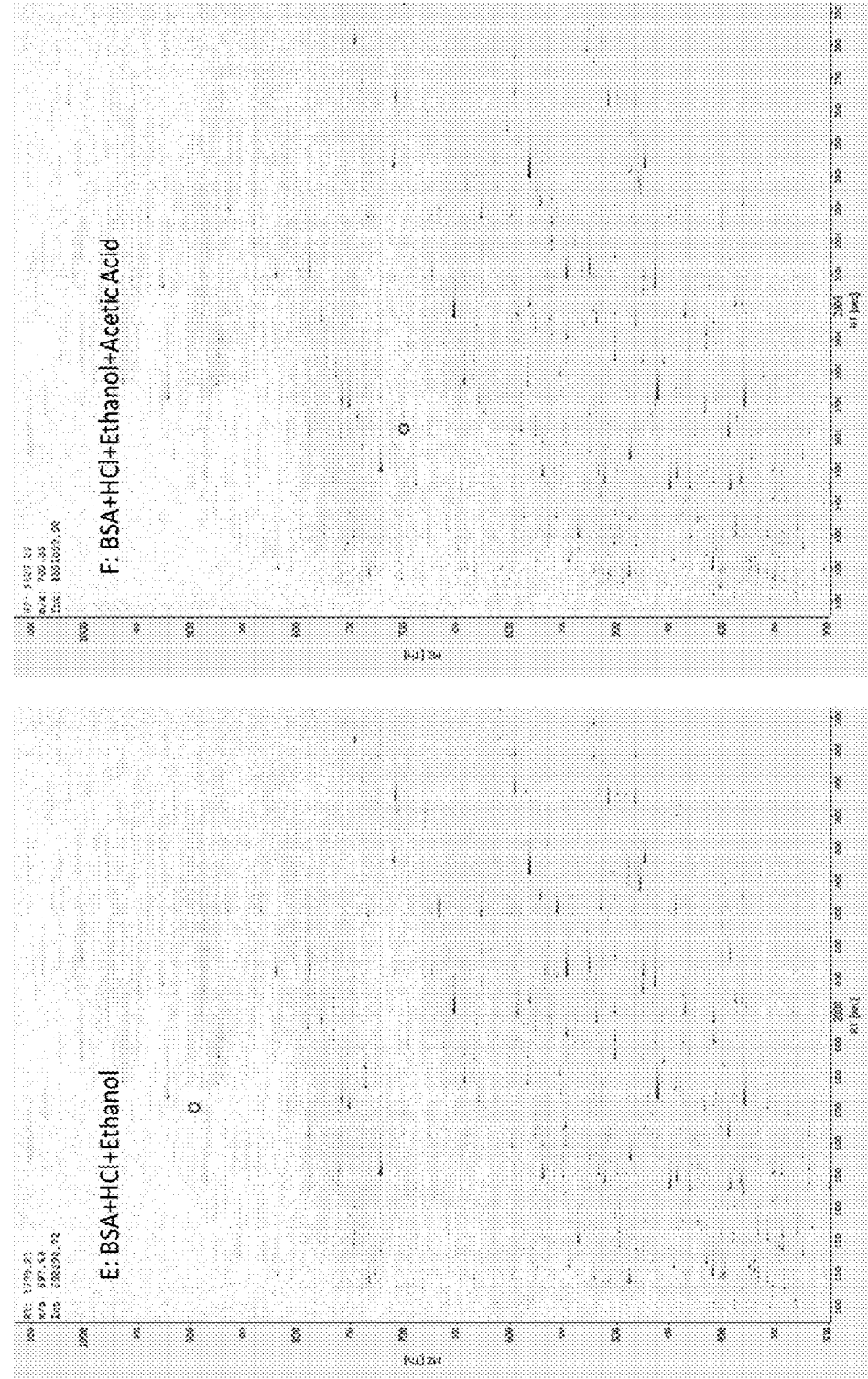
Figure 17A:
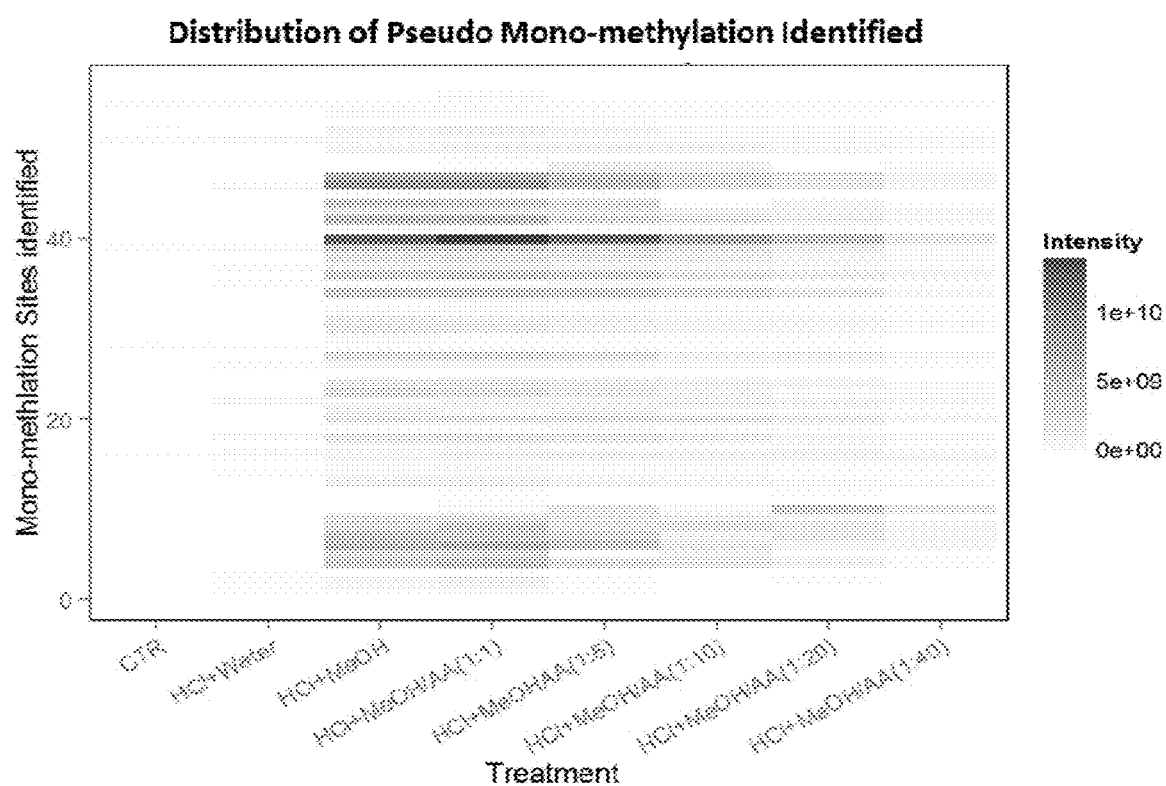
FIG. 17 shows identification quantification results demonstrating that excessive acetic acid can effectively suppress esterification. Different ratios between methanol/ethanol and acetic acid (1:1, 1:5, 1:10, 1:20, 1:40) were tested. A: Quantitative results from methyl esterification; B: Quantitative results from ethyl esterification; C: Results for unmodified peptides.
Figure 17B:
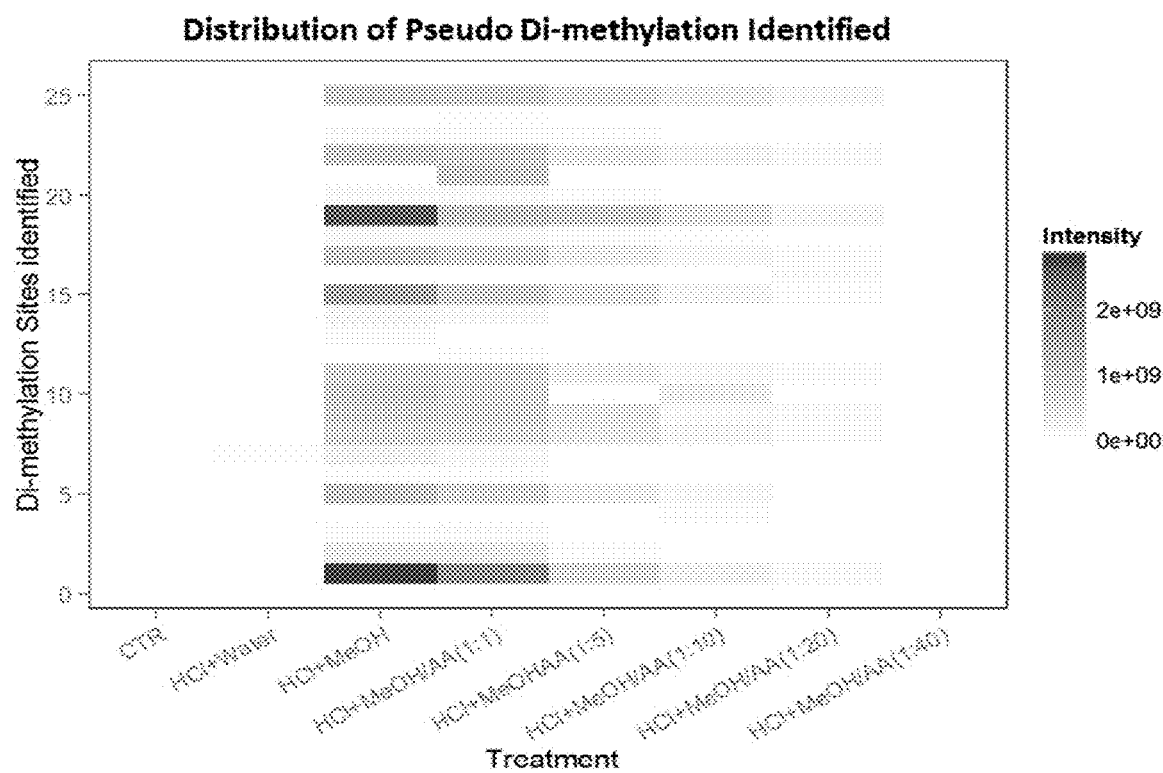
Figure 17C:
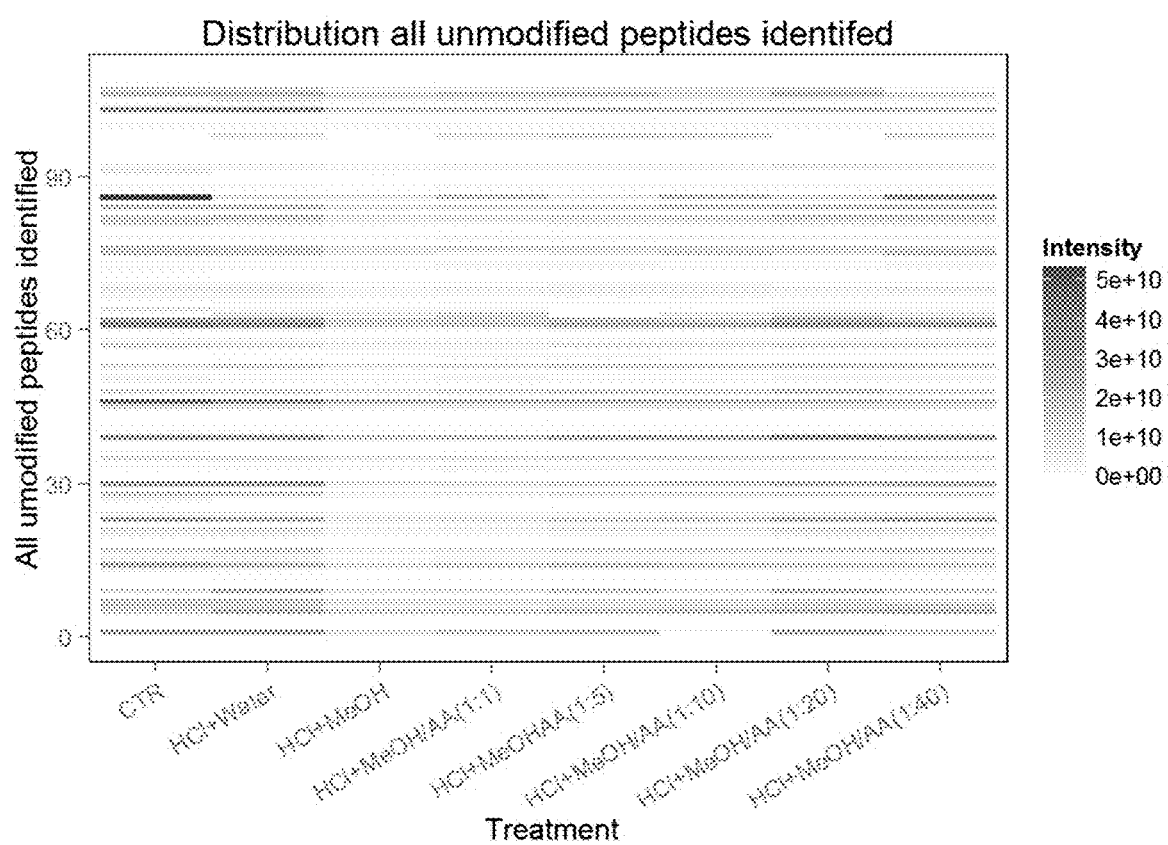

In order to increase the reaction efficiency and reduce byproduct (i.e., suppress side reactions), the standard MDA reagent was substituted with 1,1,3,3-tetraisopropoxypropane (TiPP), leading instead to the in situ production of MDA (FIG. 3). Esterification readily occurs under strong acidic conditions, and the TiPP reaction produces in situ isopropanol, which is branched and less reactive, leading to less than 2% peptide esterification. In our workflow, any form of esterification, including methyl, ethyl, and isopropanol, will lead to the false-positive identification of mono-, di- or trimethylation on adjacent targeted amino acids (e.g., arginine, lysine and histidine). To further suppress potential esterification, we pre-incubated the TiPP and HCl with an excess of acetic acid. We observed a drastic suppression of esterification on peptides following acetic acid pre-incubation (FIGS. 16 and 17). The amount of acetic acid spiked in our pre-incubation was more than sufficient to neutralize the residual alcohol from the TiPP synthesis or any other residual alcohol in the samples. Possible acetylation introduced during sample processing can be differentiated by high-resolution MS and is therefore not a concern (Zhang, K. et al., Proteomics 4: 1-10 (2004)).

Figure 4A:
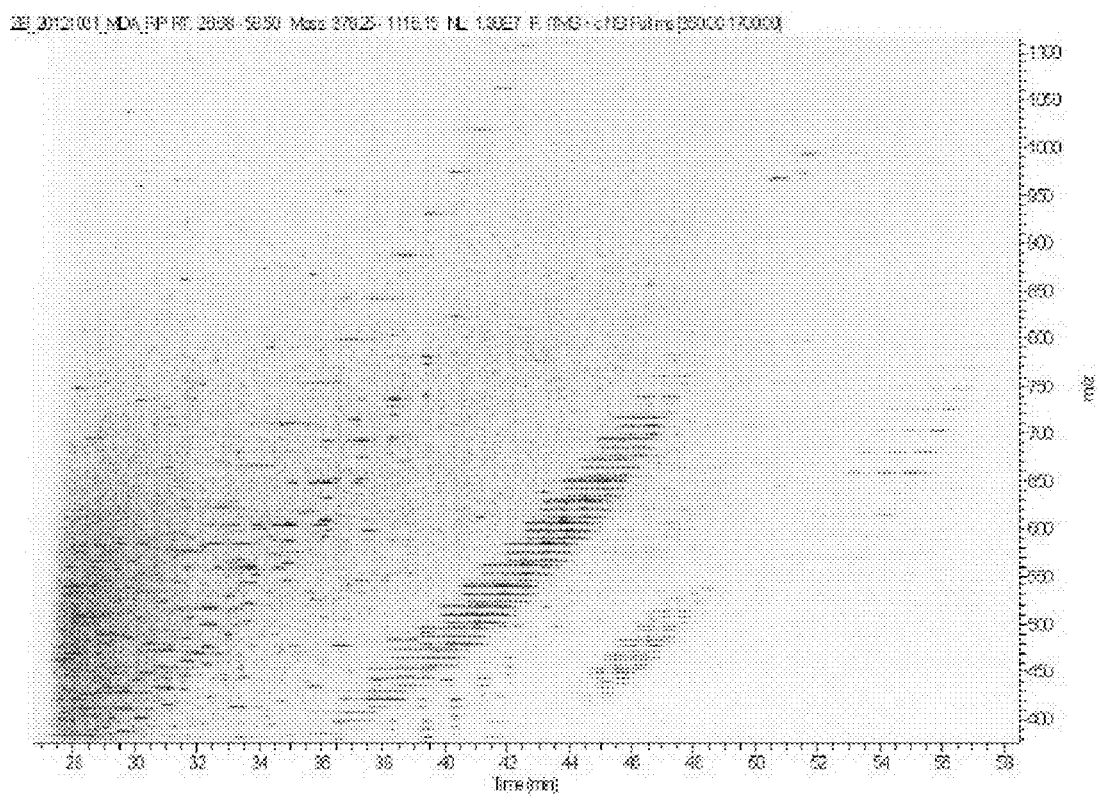
FIG. 4 shows polymers generated by the reactions in FIG. 3. A: Polymers after MDA reaction; B: Polymers after OPA reaction. The polymers are displayed in a virtual 2D map, with time and m/z. The pattern shows a typical polymer contamination pattern. The polymers are readily removed by the extraction steps in the full procedure.
Figure 4B:
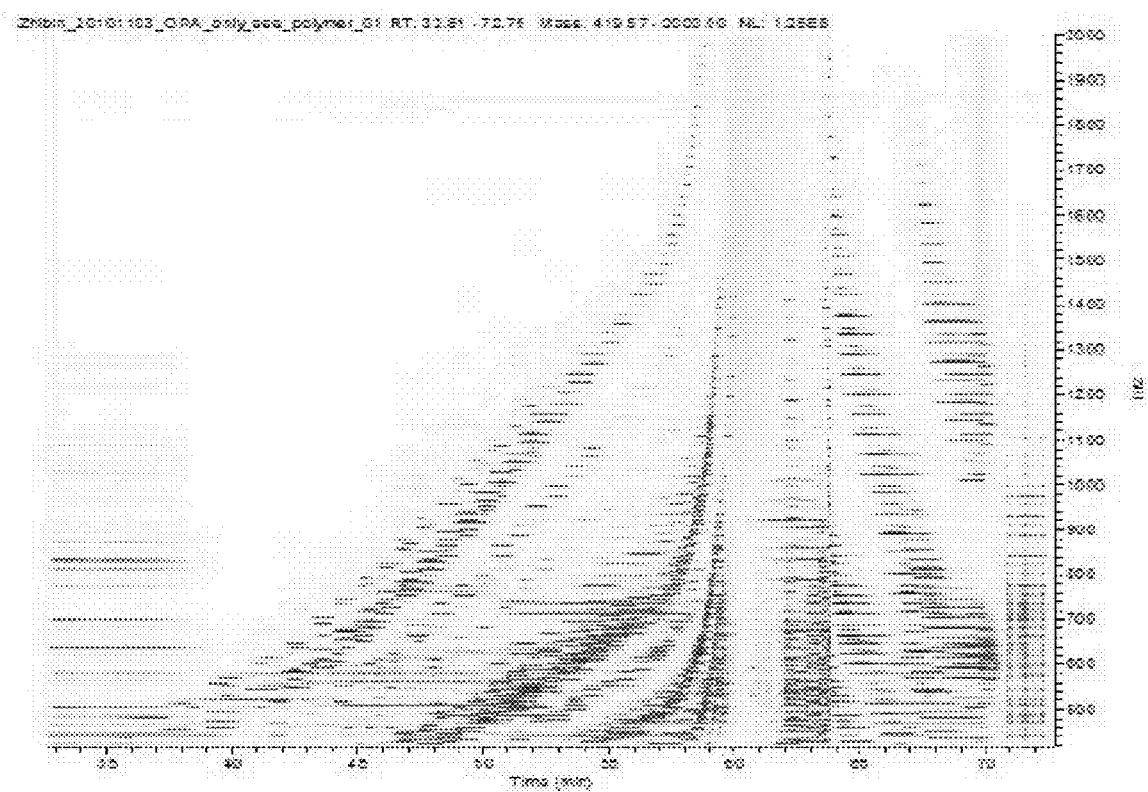
Figure 7:
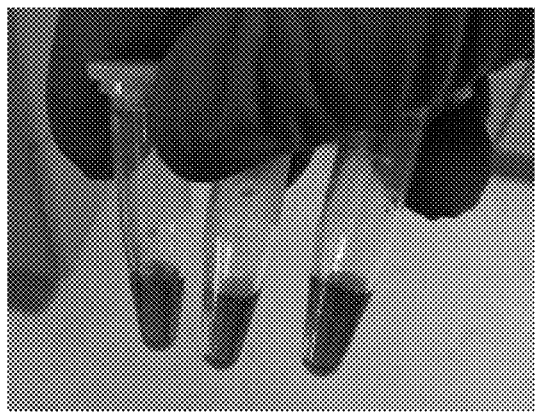
FIG. 7 shows color change brought by the MDA reaction (A) and OPA reaction (B), which can be used for quality control and as a reaction indicator. A series of 50 mM ammonium bicarbonate was added to the OPA reaction buffer.
Figure 7:
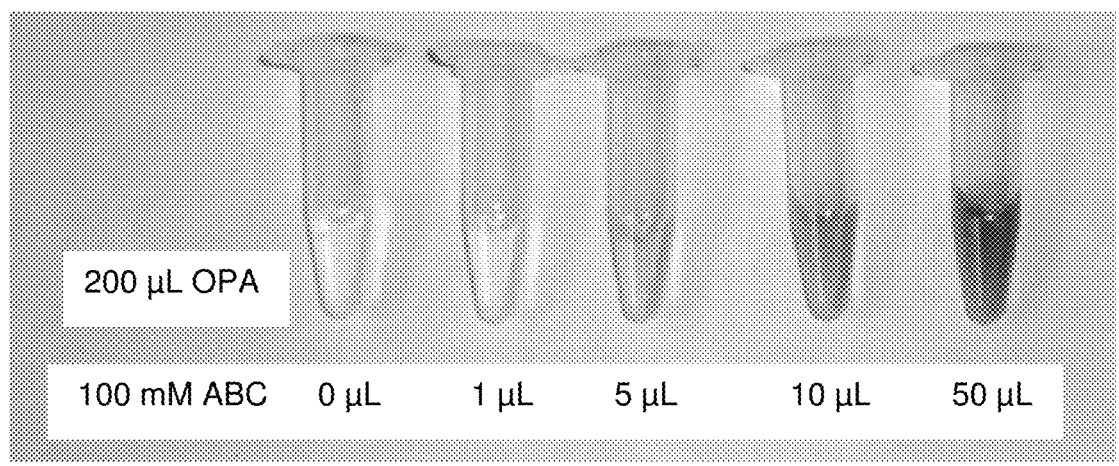

The derivatization products were subsequently purified on reverse phase/strong cation exchange (RP/SCX) solid phase extraction (SPE) columns to remove polymer byproduct (FIGS. 4A, 7A). Derivatization efficiency was tested using a tryptic digest from 10 μg of total lysate of HeLa cells. Over 98% of the arginine residues in the peptides observed by MS were modified by MDA (data not shown). This efficiency was consistent with previous reports (Foettinger, A. et al., J. Mass. Spectrom. 41: 623-632 (2006)).

The second step was to block the epsilon primary amines on un-methylated lysine residues and the free primary amines at the N-termini of peptides. Most amine-reacting chemicals used to tag or block amino groups, such as NHS reagents, react slowly with secondary amines. In our approach, only the primary amines need to be blocked, leaving methylated amines unreacted. OPA has long been used for primary amine detection and quantitation by post- or pre-column derivatization in the presence of sulfhydryl groups (Benson, J. R. & Hare, P. E., Proc. Natl. Acad. Sci. USA 72: 619-622 (1975)). In addition, methylated lysine cannot react with OPA to form a ring structure due to steric hindrance and therefore remains positively charged at neutral or high pH. The reaction of OPA with primary amines leads to the rapid production of a fluorescent intermediate (within minutes on average). The transition to the second intermediate and the final product takes longer. The reaction thus proceeds to a final stable product through two intermediates (FIG. 3).

Figure 5:
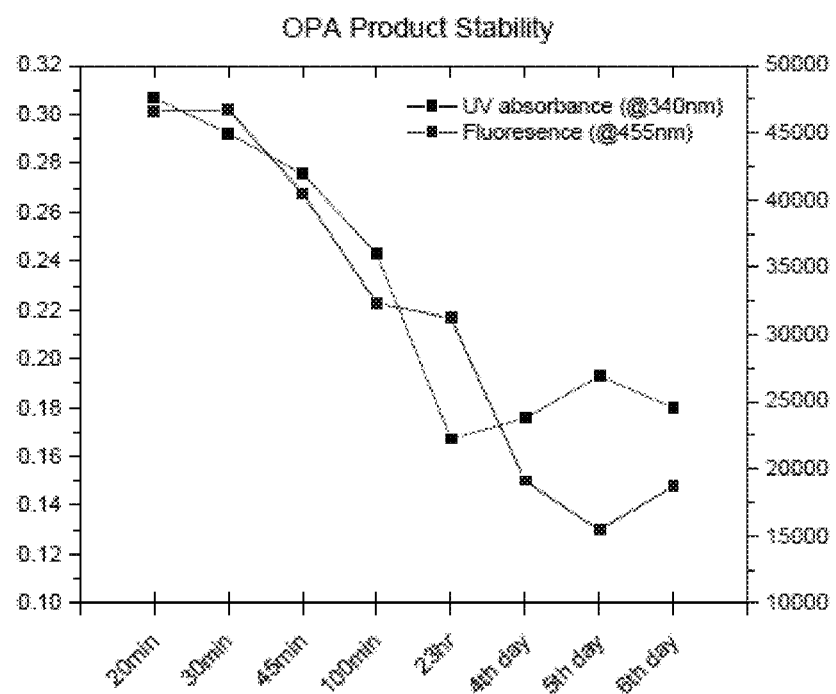
FIG. 5 shows the stability of the OPA reacted peptide product measured by 340 nm UV absorbance and fluorescence at 455 nm. A plot of 340 nm UV absorbance (black) and fluorescence at 455 nm irritated by 340 nm (blue) vs. time is shown.
Figure 6:
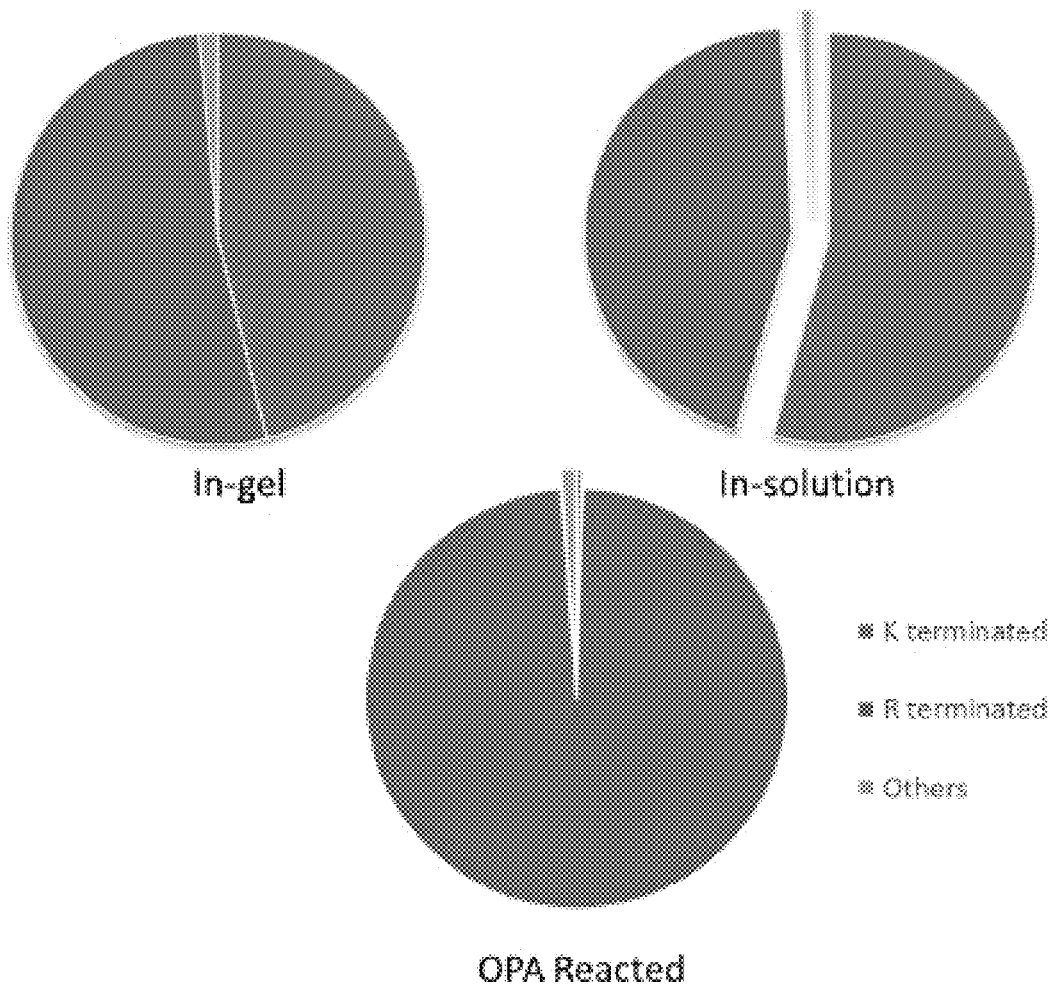
FIG. 6 shows comparison between percentage of peptides with lysine (K) (blue) and arginine (R) (red) as C-terminals from MS identification of regular proteomic profiling and OPA reacted sample. Other peptides are shown in green. In-gel and In-solution dataset were calculated based on previous datasets from multiple proteomic experiments using a standard trypsin digestion protocol.

We tested whether the OPA reaction could be applied to a complex proteomic sample. Hela protein tryptic digest was labeled with the OPA reagent to find the best reaction time. Briefly, a protein extract from Hela cells was digested with trypsin, and the resulting peptides were reacted with the OPA reagent. The reaction proceeded rapidly in the first 100 minutes, and then stabilized within 24 hours (measured by absorbance at 340 nm and emission at 455 nm from the fluorescent intermediate) (FIG. 5). In practice, the reaction was limited to two hours to reduce the exposure of the peptides to high pH (e.g., pH 10.5). To our knowledge, this represents the first example of large-scale proteomic profiling using the OPA reaction with a complex peptide mixture, with the non-fluorescent modification of $C(8)H(4)O$ (mass shift of 116.02 Da) rather than the fluorescent modification (mass shift of 176.02 Da) (FIGS. 1, 3B). We confirmed that the non-fluorescent product with modification of $C(8)H(4)O$ (mass shift of 116.02 Da), instead of the fluorescent product (with mass shift of 176.02 Da) was stable and suitable for MS identification (FIG. 3B). Technically, lysine-terminated tryptic peptides can be fully modified on both C-terminal lysine and N-terminus by OPA, and therefore have their charges reduced. This is illustrated by the very low number of lysine terminated peptides identified in our dataset, where over 98% of the peptides observed from a complex peptide mixture subjected to the OPA reaction were terminated with an arginine residue. As well, less than 0.5% were terminated by un-modified lysine residues (FIG. 6). Most of the peptides with lysine at the C-terminus were OPA modified on both the N and C termini, resulting in the elimination of positive charges and subsequent failed MS identification. In contrast, a typical MS profiling from an untreated tryptic peptide mixture leads to about 1:1 ratio of lysine or arginine residue terminated peptides (Olsen, J. V. et al., Mol. Cell. Proteomics 3: 608-614 (2004)). These results showed the high OPA labeling efficiency on peptide mixtures and at the proteomics level.

Example 2. Detection of Methylated Protein in a Mixture

Following optimization, we tested whether these two chemical reactions could be combined in a workflow for the charge-based negative enrichment of methylated peptides based on the fact that the methylated arginine and lysine side chains do not react with MDA-OPA. Briefly, samples were first subjected to the MDA reaction followed by the OPA reaction. Prior to the OPA reaction, the MDA products were purified and reconstituted in the OPA buffer. The final products were then subjected to SCX fractionation by pH-step elution before MS analysis (FIG. 1).

We tested whether a standard methylated protein could be detected in a complex mixture using the optimized workflow described above. Briefly, intact bovine serum albumin (BSA) protein was chemically methylated using a dimethylation strategy previously described (Kleifeld, O. et al., Nat. Biotechnol. 28: 281-288 (2010)) to introduce mono- and dimethylation on lysine at the protein level. Mass spectrometry (MS) analysis of digested, modified BSA revealed a series of methylations on lysine (data not shown). One microgram of the methylated BSA was spiked into 1 mg of HeLa total lysate and the mixture was processed using our workflow. Out of 915 MS features, 9 had BSA methylation events, representing 4.2% of total ion intensity (which roughly represents the total sample quantity) of all identified peptides (data not shown). In contrast, control analysis of the original mixture did not give any peptides corresponding to the methylated form of BSA, i.e., no methylation events from BSA were identified.

Figure 1B:
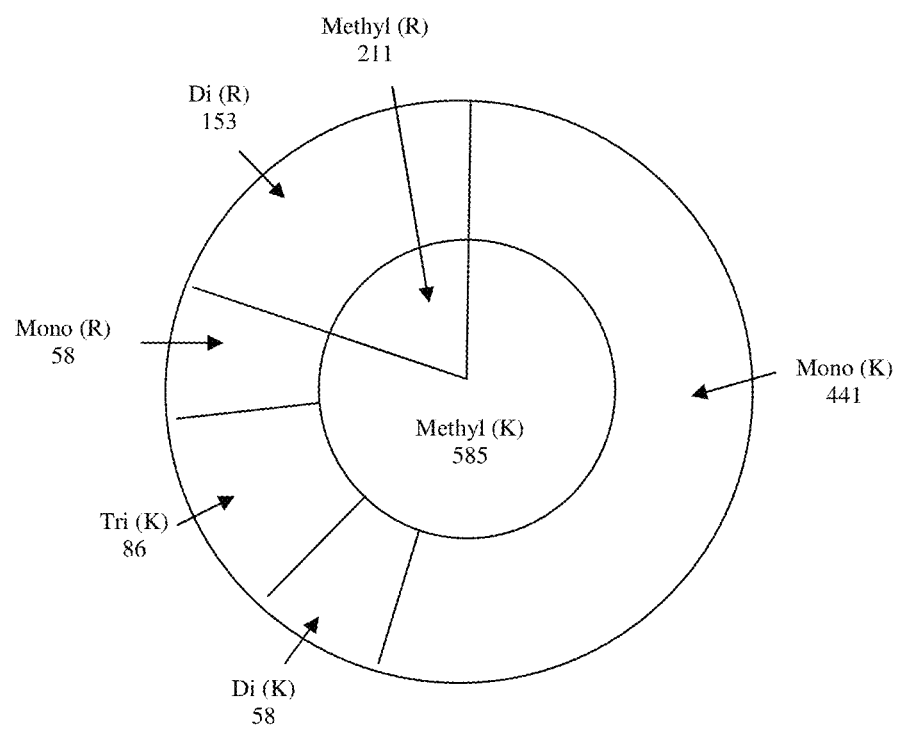
Figure 8:
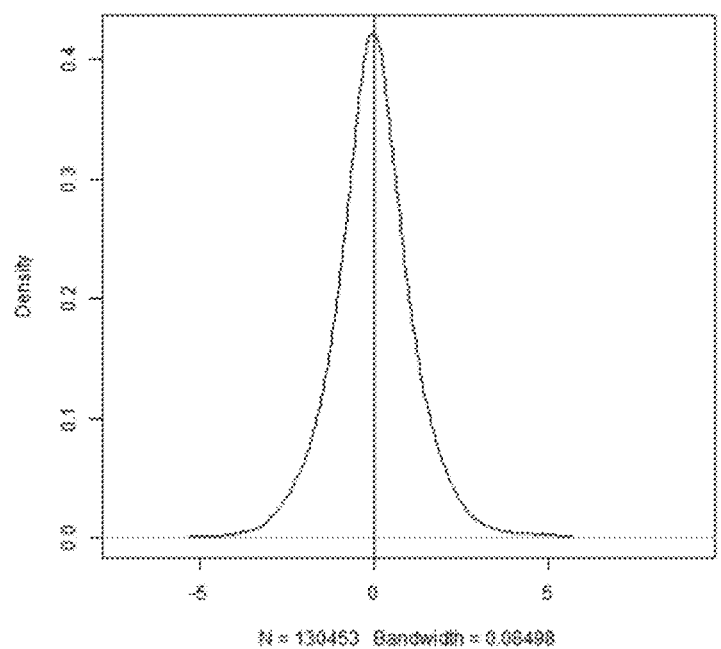
FIG. 8 shows the MS accuracy in ppm of MS1 and MS2 on Q-Exactive. A: MS1 level; B: MS2 level. Data in (C) shows that the masses of the identified peptides were within a tolerance of less than 4 ppm, which is sufficient to differentiate N-acetylation from trimethylated lysine.
Figure 8:
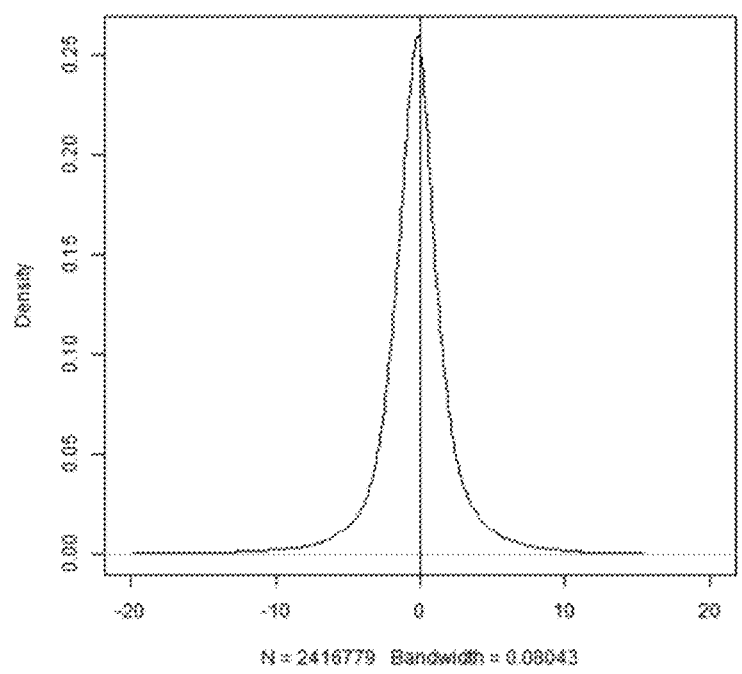
Figure 8C:
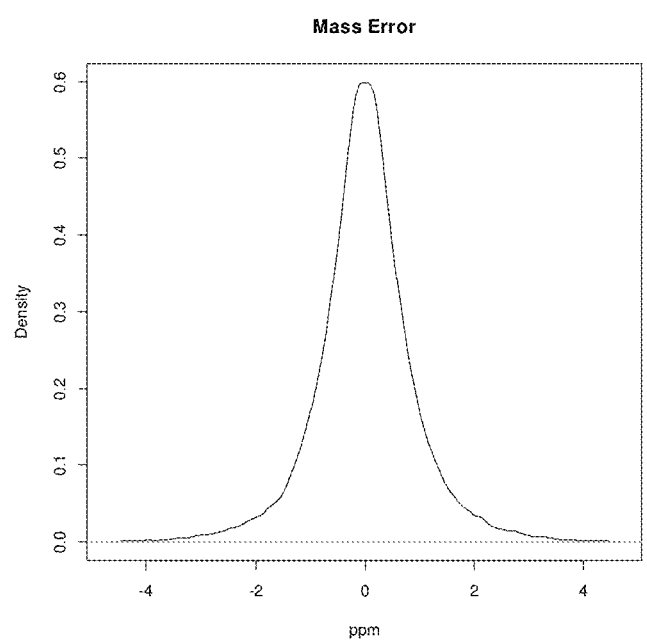
Figure 9A:
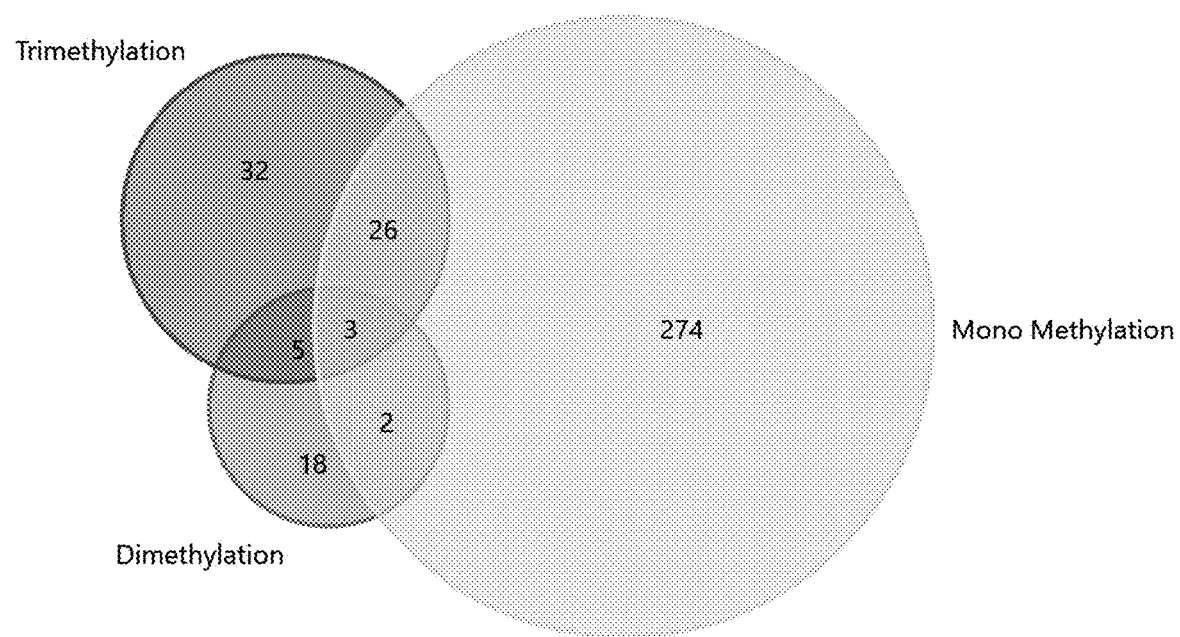
FIG. 9 shows methylation event overlap between mono, di, and tri methylated lysine (A) as well as mono and di methylated arginine (B), indicating that methylation events can overlap on the same amino acid.
Figure 9B:
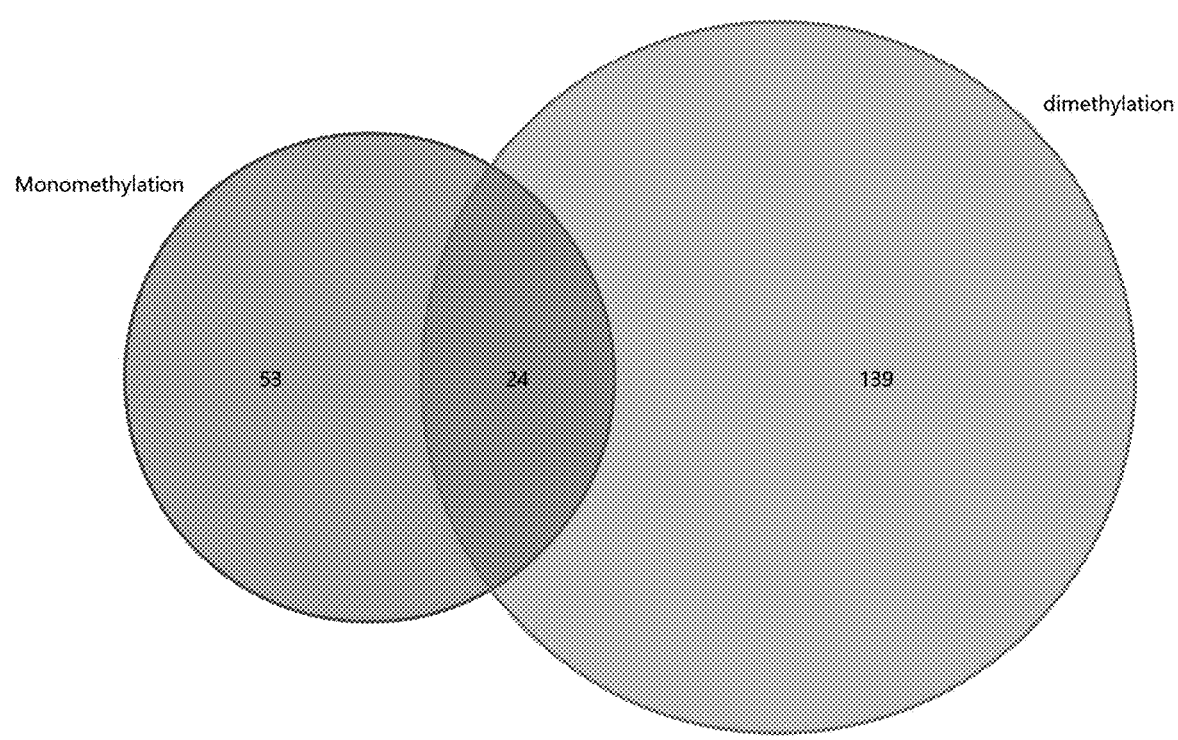
Figure 18:
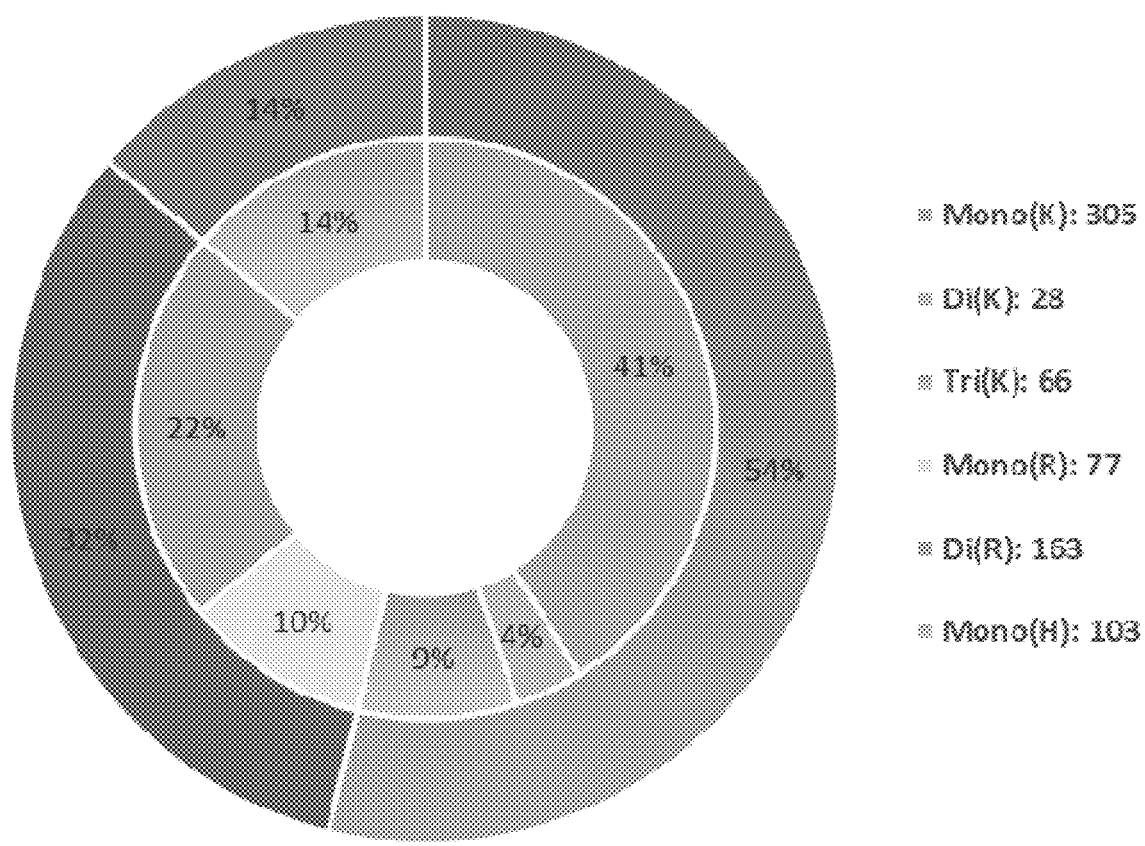
FIG. 18 shows a summary of identified methylation site profile for lysine, arginine, and histidine.

We then tested whether this strategy could be applied for large scale profiling of protein methylation. HEK 293 cell lysates (500 μg) were processed through our workflow and analyzed by high-resolution MS and MS/MS (HCD mode) on a Q-Exactive mass spectrometer. We identified 1413 methylation events using an overall 1% FDR filtering. 793 methylation events met an even more stringent requirement of 1% FDR for each methylation status (data not shown). Of the 793 unique methylation events, 209 and 584 were observed on arginine residue and lysine residues, respectively (FIGS. 1B, 9; see also FIG. 18, which shows results from another run, in which 742 methylation events from two enrichment analyses of the 500 μg HEK293 total lysate as starting material were identified, including 399, 240, and 103 methylation events observed on lysine, arginine, and histidine, respectively). It is noted that the number of methylation events is conservative considering that we used 1% site-specific FDR filtering in MaxQuant (Cox, J. et al., J. Proteome Res. 10: 1794-1805, 2011) and removed all C-terminal trimethylation events. Furthermore, our MS/MS spectra were obtained using high-collision dissociation (HCD) mode followed by detection on an Orbitrap mass analyzer and had an average mass deviation lower than 10 ppm for peptide fragments (FIG. 8). The high mass accuracy of the parent and fragment ions reduced the size of the search space and therefore greatly reduced the FDR (Cox, J. et al., J. Proteome Res. 10: 1794-1805 (2011)). Parent mass of the peptides was measured with a mass tolerance of 7 ppm or lower, which is sufficient to differentiate N-acetylation from tri-methylated lysine (Zhang, K. et al., Proteomics 4: 1-10 (2004)). The high mass accuracy of the parent and fragment ions reduced the size of the database search space and therefore greatly reduced false peptide spectra matches. The masses of the identified peptides were within a tolerance of less than 4 ppm (FIG. 8C), which is sufficient to differentiate N-acetylation from trimethylated lysine (Zhang, K. et al., Proteomics 4:1-10, 2004).

Figure 2A:
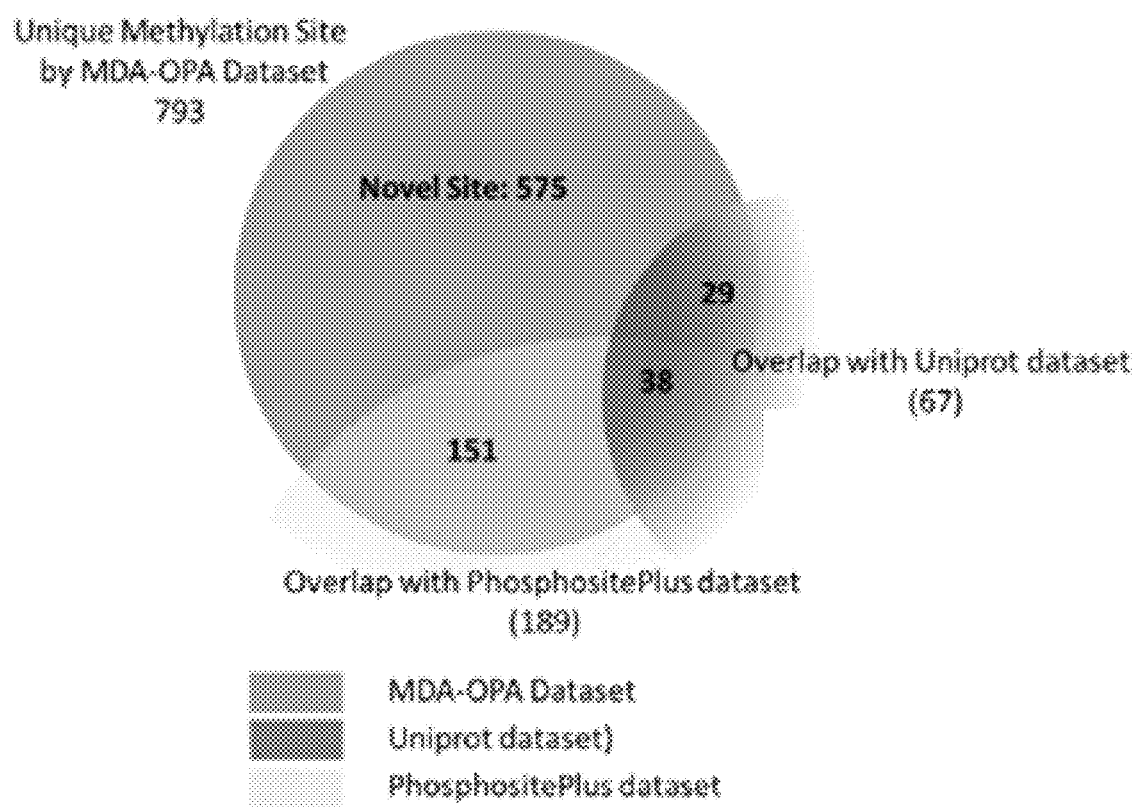
FIG. 2 shows the following: A: Comparison of our methylation results with the database of protein methylation in PhosphositePlus and Uniprot, in one embodiment. B: Icelogo visualization of six flanking amino acids around methylation events. Sequences were aligned at methylated amino acid residues in the middle. Over-represented (above) and under-represented (below) amino acids are shown against the human proteome with p<0.05. C: Pfam protein domain analysis of identified arginine methylated proteins. D: Pfam protein domain analysis of identified lysine methylated proteins. E: Motif-X extraction of the consensus sequence pattern for mono-methylation on lysine and di-methylation on arginine residues.
Figure 2B:
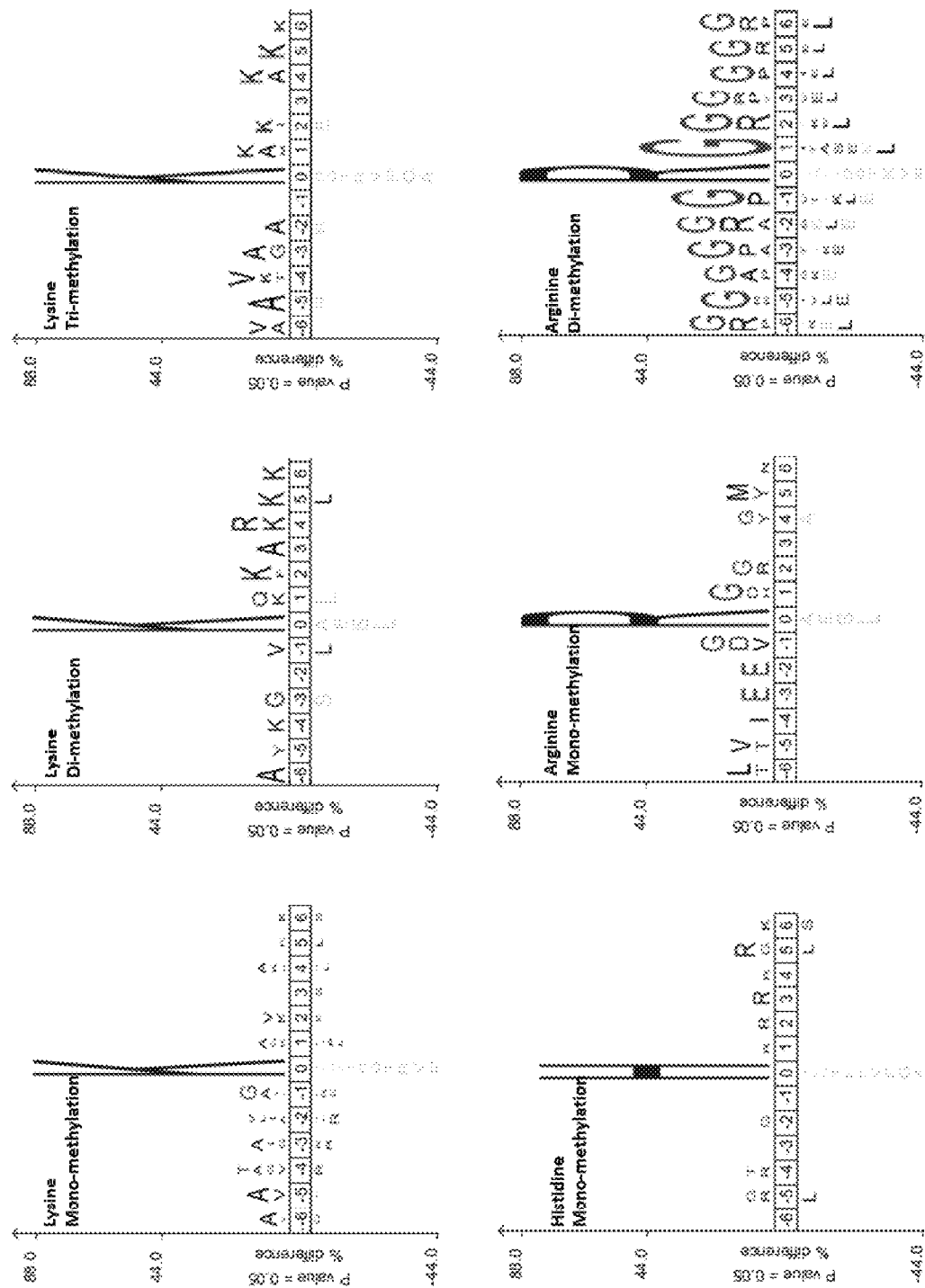
Figure 2C:
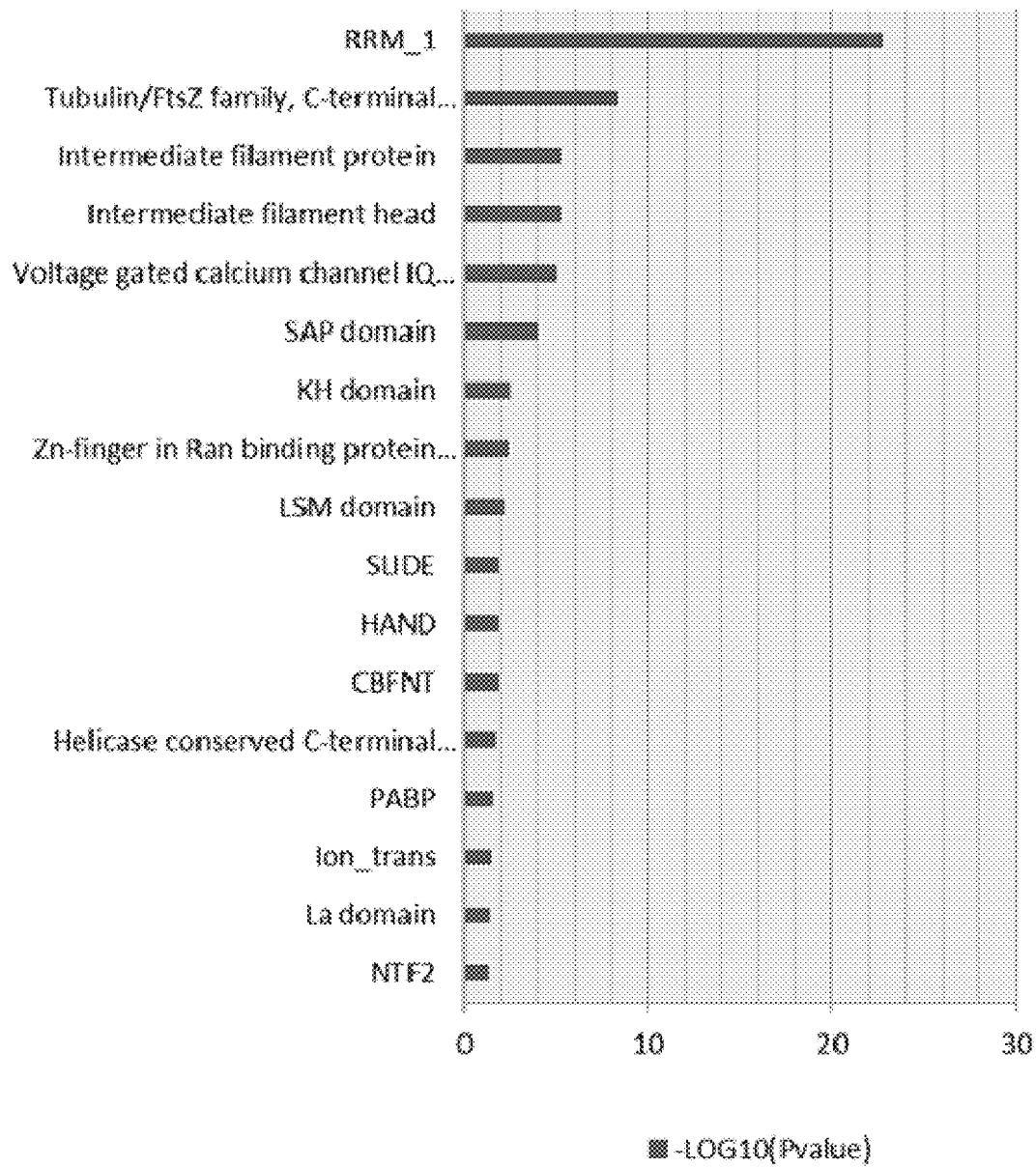
Figure 19:
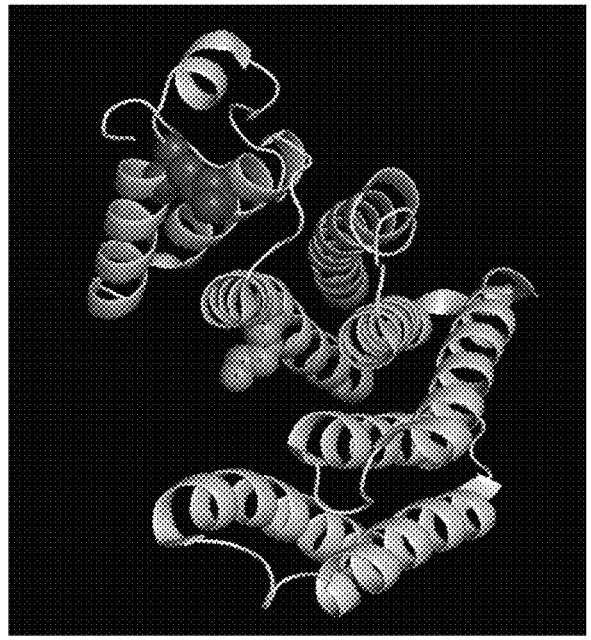
FIG. 19 shows examples of surface accessibility of methylated amino acid in one embodiment. A: 14-3-3 protein theta (Uniprot: P27348). Red: K3 with trimethylation identified; Green: K49 with mono-methylation identified. B: Triosephosphate isomerase (Uniprot: P60174). Red: K106 with mono-methylation identified. Green: K212 with mono-methylation identified.
Figure 19:
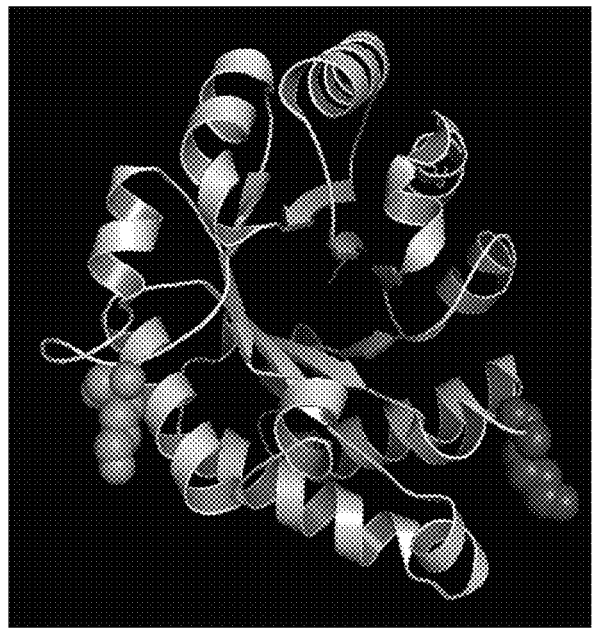

PTM sites are generally located on the protein surface, especially methylation and ester-linked phosphorylation. Protein surface accessibility analysis showed a significant enrichment of methylated RK residues on the protein surface (p=6.3e-47, against all amino acids of methylated proteins as the background). For example, of the novel methylation events in our dataset, in one experiment trimethylation on K3 and monomethylation on K49 of 14-3-3 theta (UniProt P27348) and monomethylation on K106, K212 of triosephosphate isomerase (UniProt P60174) were all located on the protein surface (FIG. 19). Databases of protein methylation events are limited compared with other PTMs such as protein phosphorylation. However, 23% of our 742 identified methylation events were present in PhosphositePlus (version Nov. 16, 2015, which includes the dataset from Guo, A. et al., Mol. Cell Proteomics, 13: 372-387, 2014) (FIG. 20d). The UniProt database has a relatively conserved and high-quality protein methylation collection, and 60 methylation events overlapped with our methylation list, including the recapitulation of known histone methylation events. Motif analysis of the flanking sequences surrounding the methylated amino acids revealed a RGG-rich motif for arginine methylation (FIG. 19). In contrast, lysine methylation did not show such a strong sequence consensus. Pfam protein domain analysis also showed significant enrichment of the RNA recognition motif RRM_1 (FIGS. 2C, D). A few lysine and arginine residues showed multiple methylation types, highlighting the dynamic regulation of protein methylation.

Figure 1C:
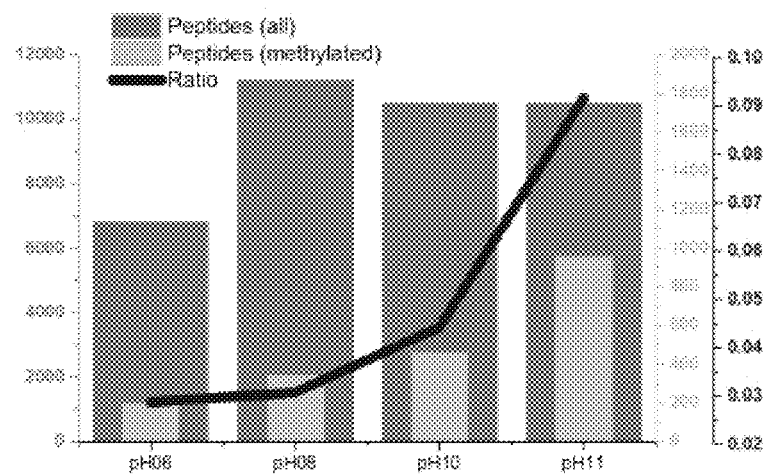
Figure 1D:
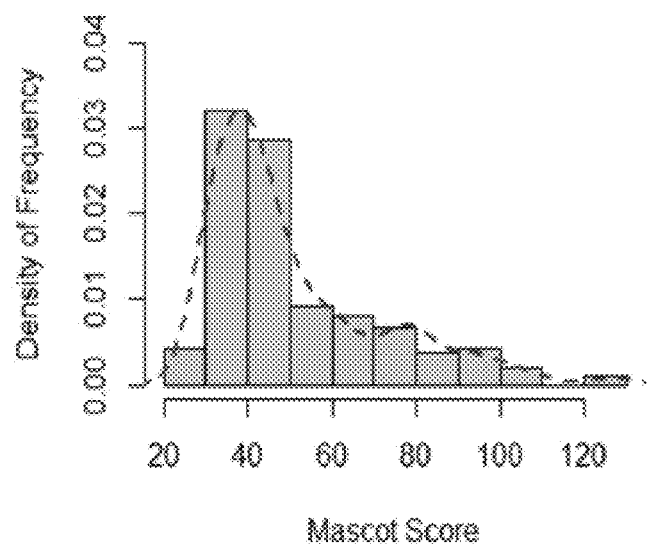
Figure 1E:
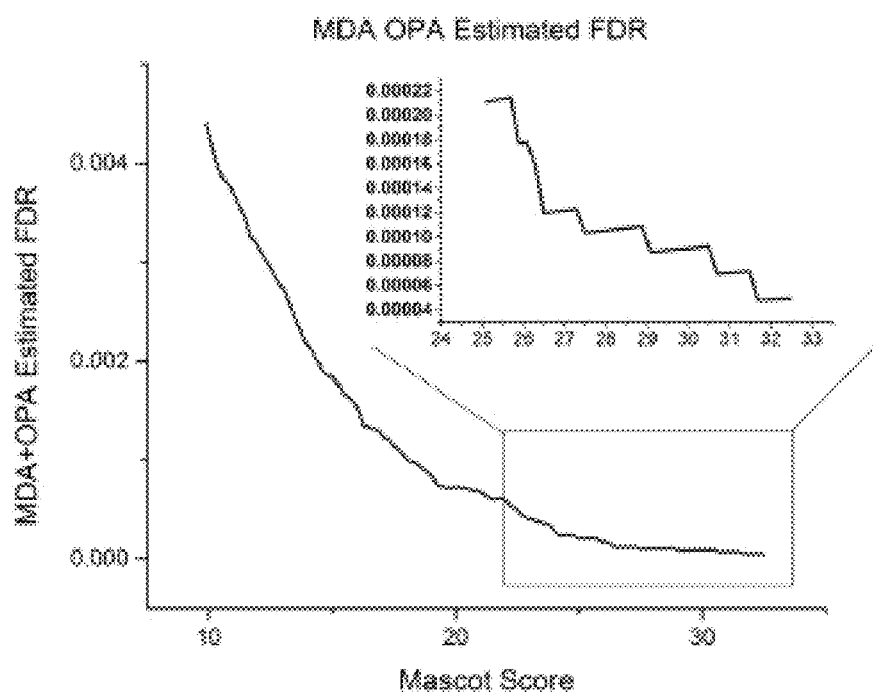
Figure 1F:
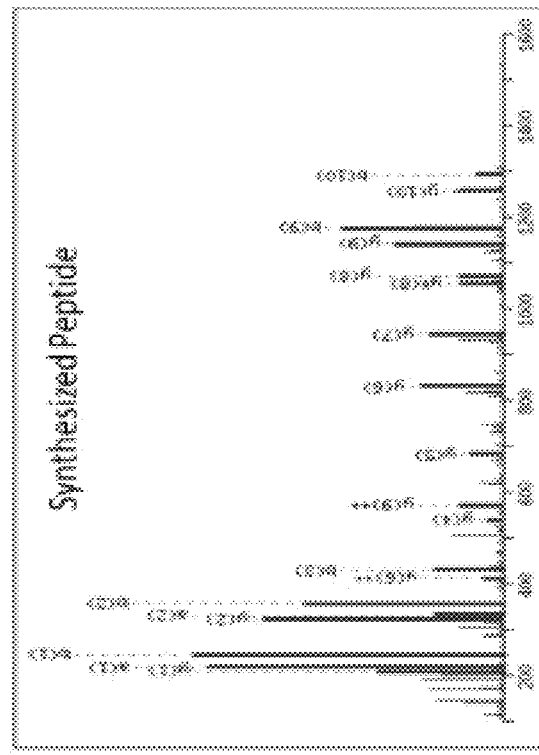
Figure 1F:
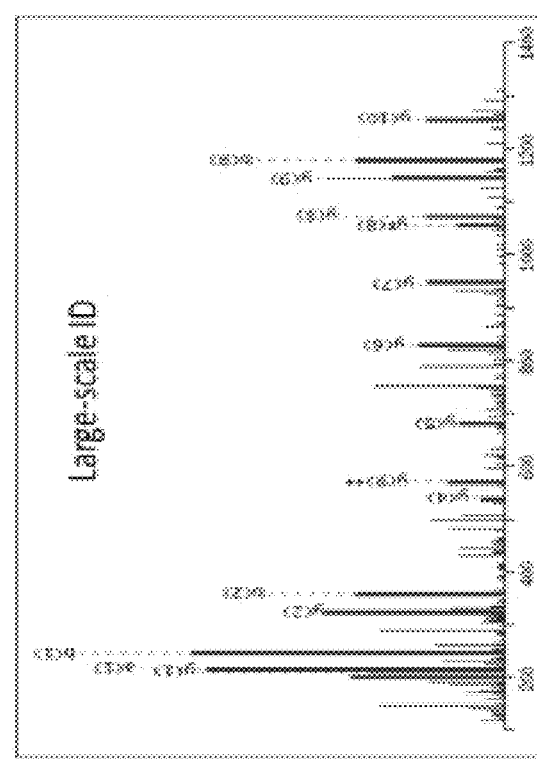
Figure 1G:
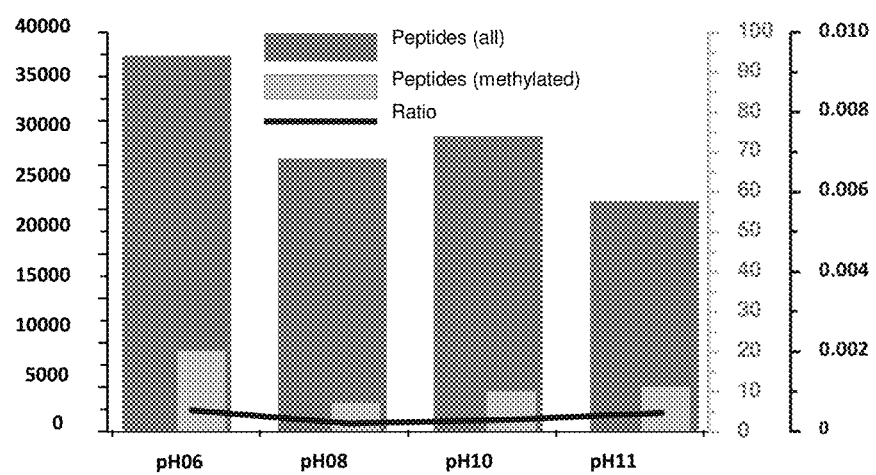
Figure 20A:
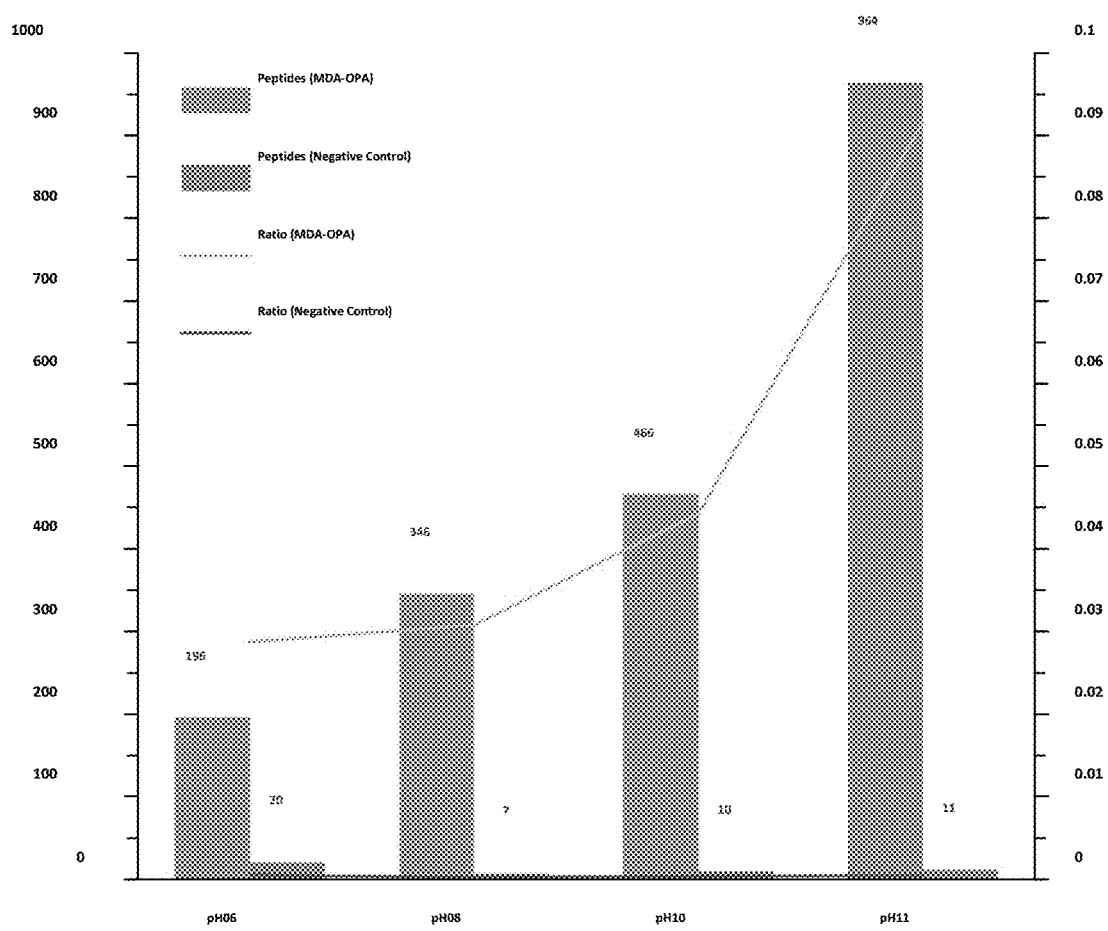
FIG. 20 shows validation and application of the MDA-OPA workflow in one embodiment. a: Methylation enrichment among SCX fractions is presented as the ratio of methylated peptide against all identified peptides from 3% to 9% in an MDA-OPA experiment, while the negative control only produced negligible methylation identification; b: The estimated FDR for methylation identification introduced by the MDA-OPA modification during database search is shown; c: Spectra validation of peptide EIAQDFK(Methyl)TDLR from large-scale identification and synthesized peptide analysis is shown. Matched fragment ions are highlighted in bold; d: Overlap of methylation events identified by the MDA-OPA workflow with the database of protein methylation in PhosphositePlus and UniProt is shown.

As expected, the specificity, represented by the percentage of methylated versus un-methylated peptides, increased with increasing elution pH (pH 6, 8, 10, and 11) of the fractions, not seen in the control experiment (FIGS. 20a, 1C, 1G). The increasing profile reinforced our confidence in the identification of methylated peptides, as false positives were expected to be randomly distributed across all pH fractions.

Figure 20B:
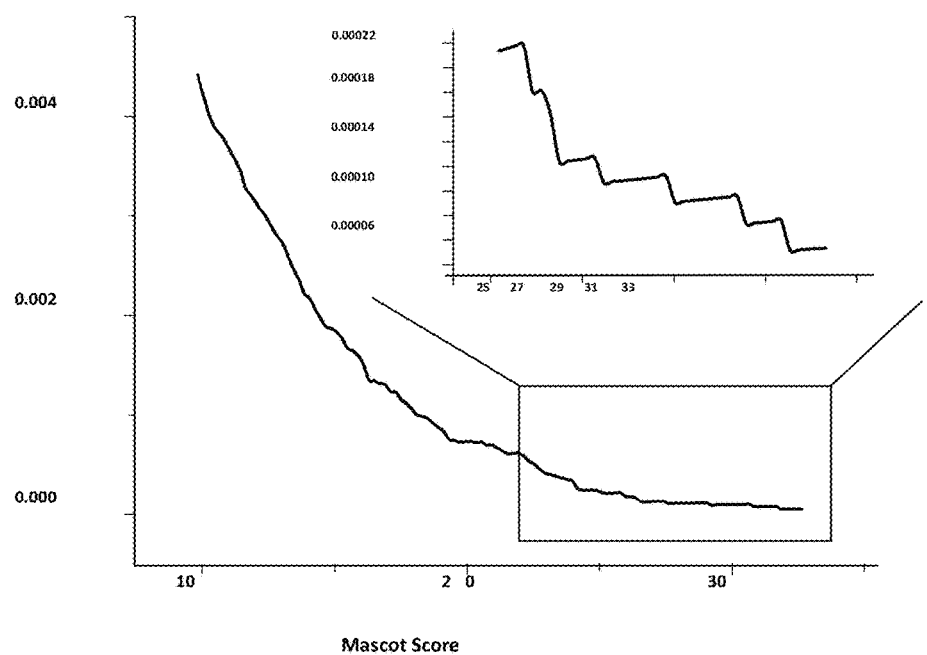

The false discovery rate (FDR) of the methylation identification introduced by multiple variable modification for MDA or OPA modifications during a database search was negligible (lower than 0.0002%; FIG. 20b). It has to be noted that we still identified un-methylated peptides. Histidine-containing peptides were also significantly enriched using our workflow ($42\pm5\%$ of identified enriched peptides) compared with a conventional proteomics workflow ($25\pm5\%$). Our results are consistent with a previously reported charge-based peptide fractionation method (Sanchez, A. et al., Proteomics 6: 4444-4455 (2006)). Histidine is the third basic amino acid after arginine and lysine, with a side-chain pKa of 6, but is not blocked in our workflow.

Figure 10:
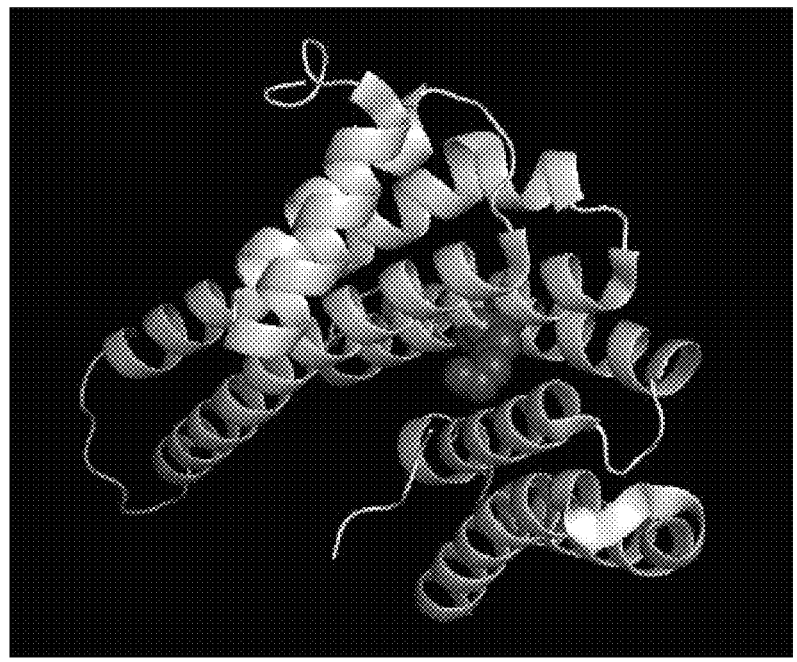
FIG. 10 shows examples of surface accessibility of methylated amino acid in one embodiment. A: 14-3-3 protein sigma (Uniprot P31947) K122 mono- and tri-methylation; B: 14-3-3 protein theta (Uniprot: P27348). Red: K139 mono-methylation. Green: K212 mono-methylation; C: Triosephosphate isomerase (Uniprot: P60174). Red: K186 mono-methylation. Green: K106 mono-methylation. Yellow: K256 mono- and tri-methylation.
Figure 10:
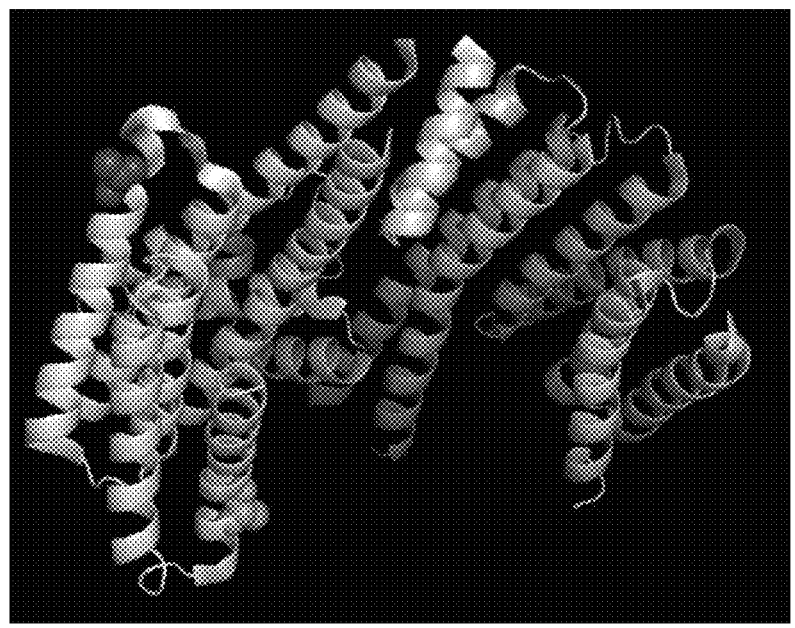
Figure 10C:
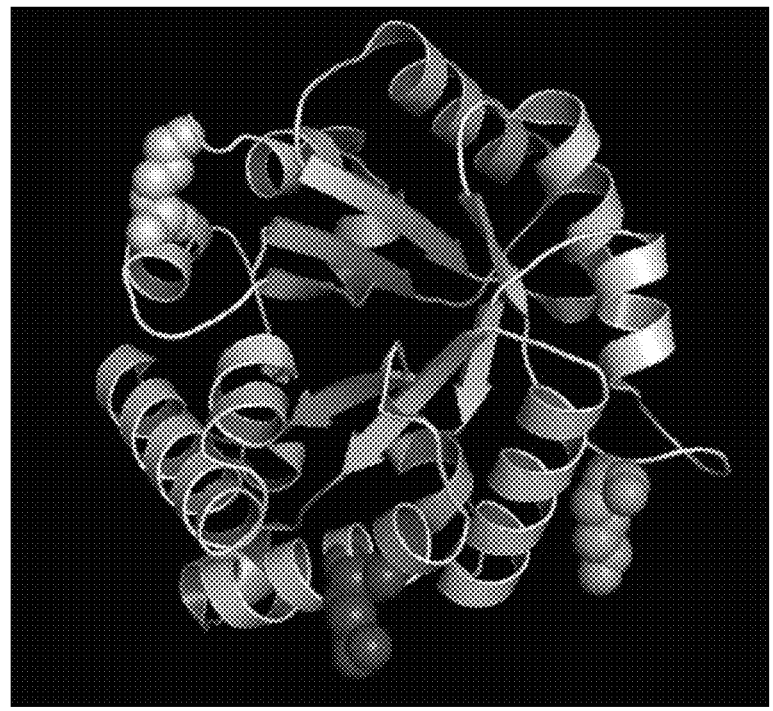
Figure 11A:
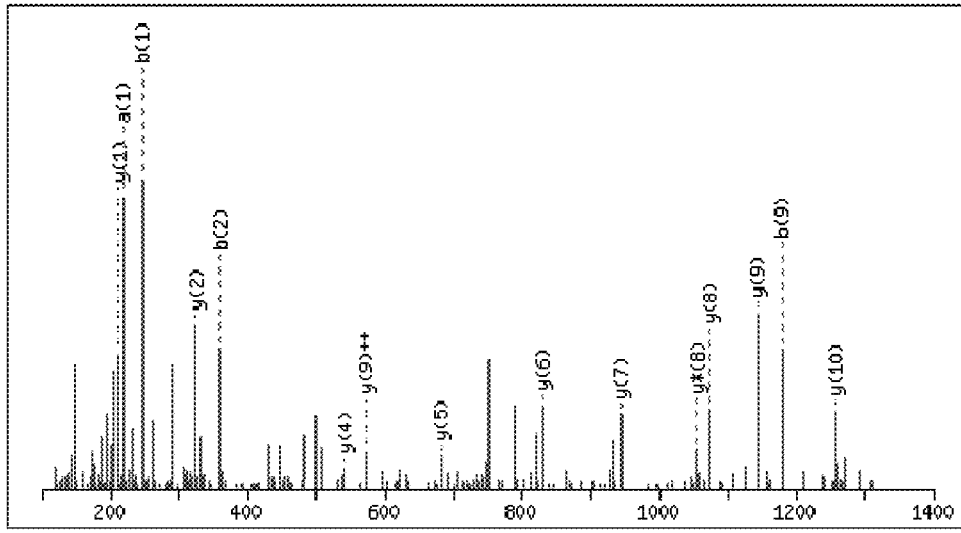
FIG. 11 shows MS/MS spectra for Peptide 1 (R.$EIAQDFK&TDLR#.F). A: Spectrum from Large scale ID and accompanying data; B: Spectrum from Validation and accompanying data.
Figure 11B:
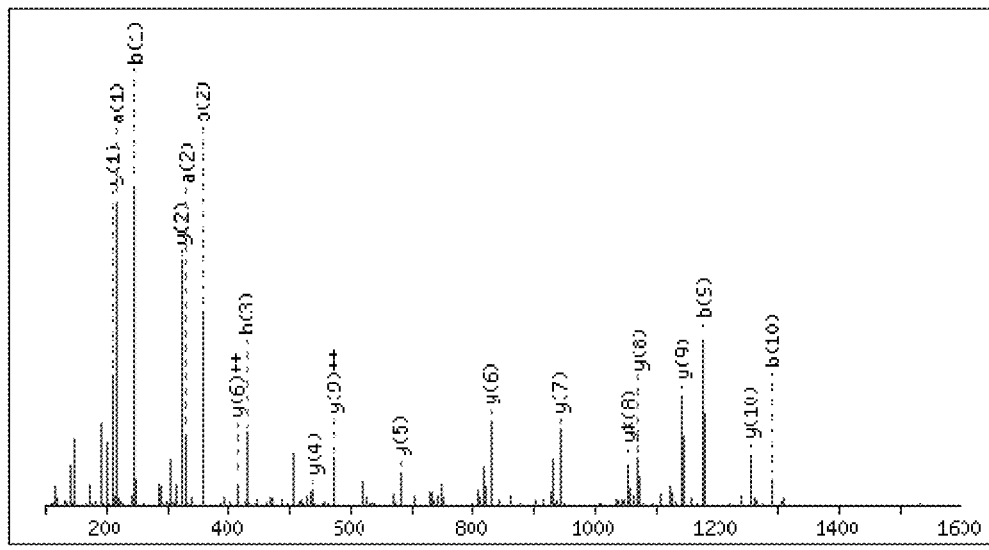
Figure 12A:
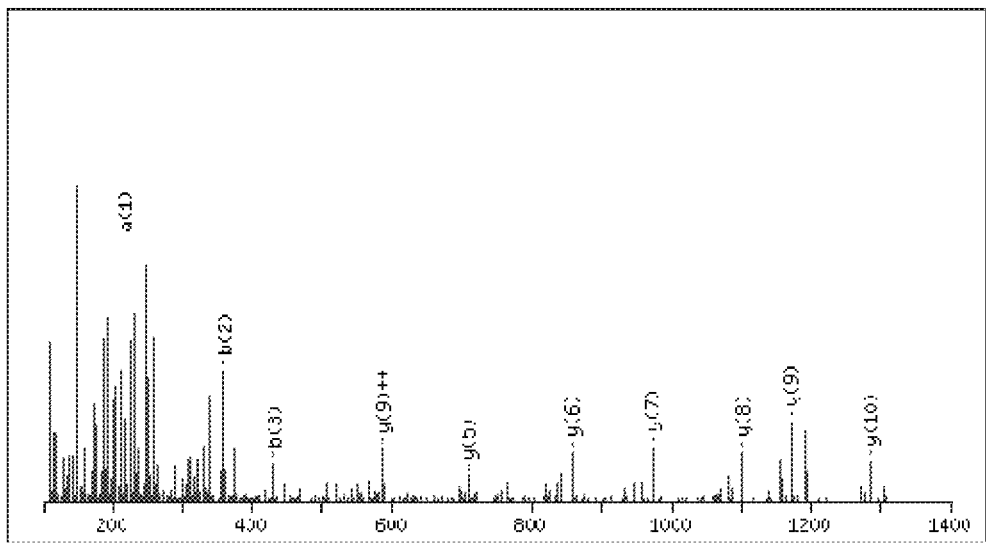
FIG. 12 shows MS/MS spectra for Peptide 2 (R.$EIAQDFK^TDLR #.F). A: Spectrum from Large scale ID and accompanying data; B: Spectrum from Validation and accompanying data.
Figure 12B:
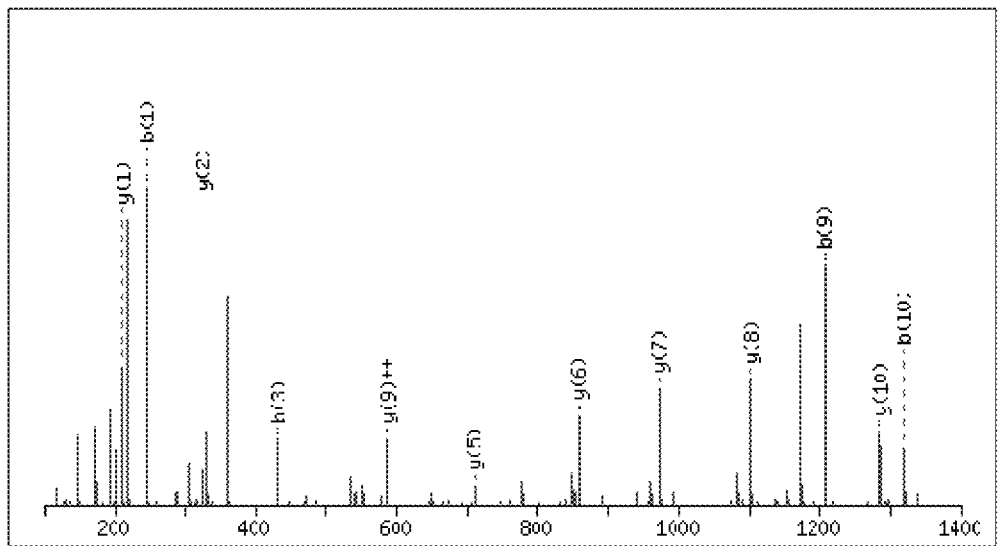
Figure 13:
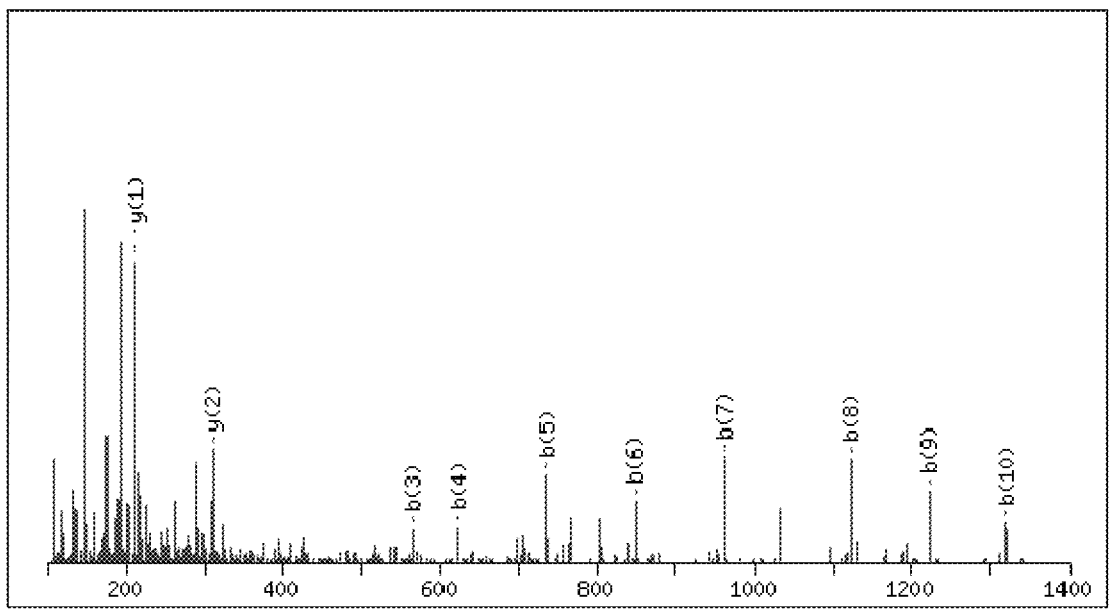
FIG. 13 shows MS/MS spectra for Peptide 3 (K.$QYK@GIIDCVVR#.I). A spectrum from Large scale ID and accompanying data are shown.
Figure 14A:
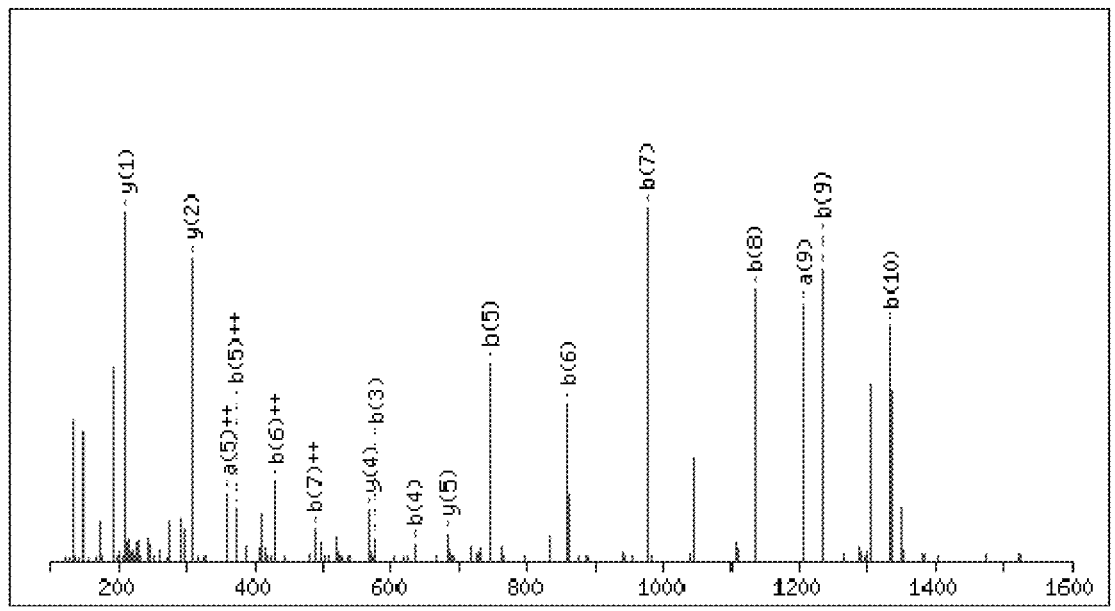
FIG. 14 shows MS/MS spectra for Peptide 4 (K.$QYK^GIIDCVVR#.I). A: Spectrum from Large scale ID and accompanying data; B: Spectrum from Validation and accompanying data.
Figure 14B:
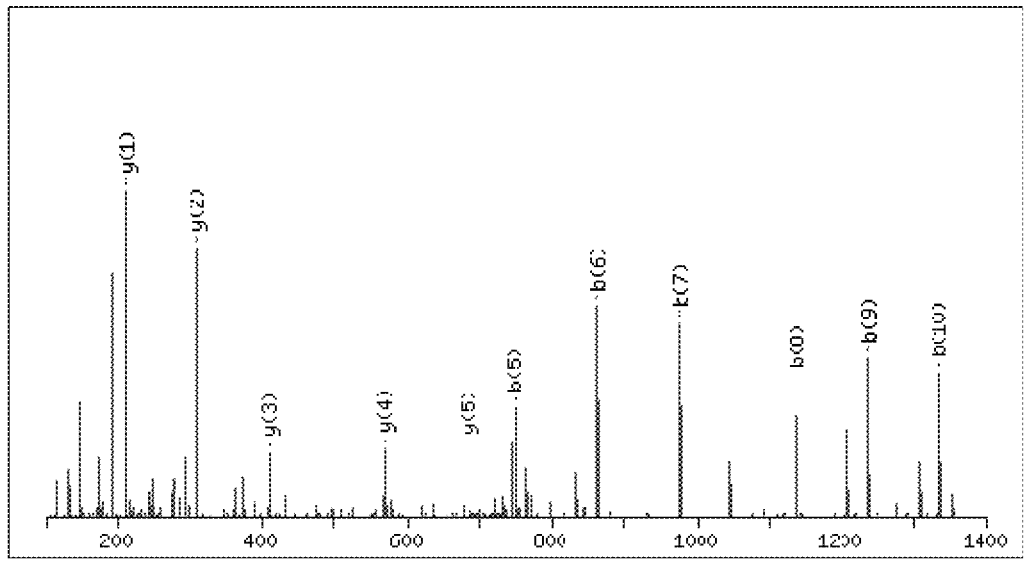
Figure 15A:
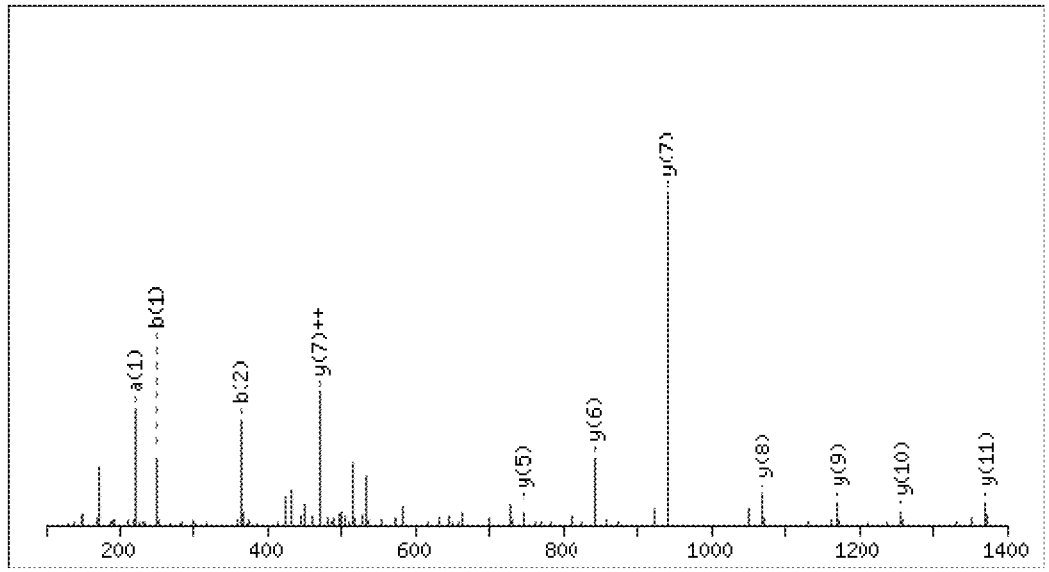
FIG. 15 shows MS/MS spectra for Peptide 5 (K.$MDSTEPPYSQK@R#.Y). A: Spectrum from Large scale ID and accompanying data; B: Spectrum from Validation and accompanying data.
Figure 15B:
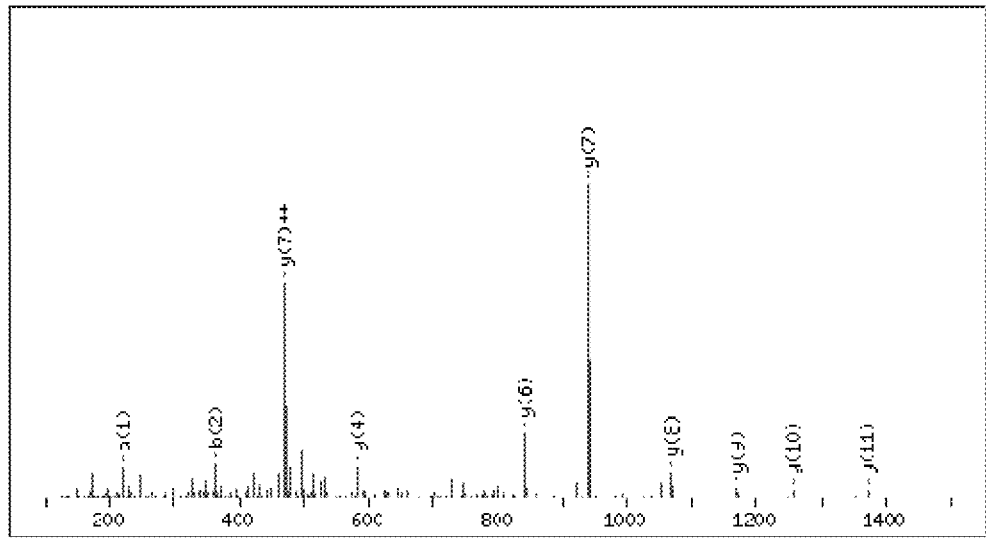
Figure 20C:
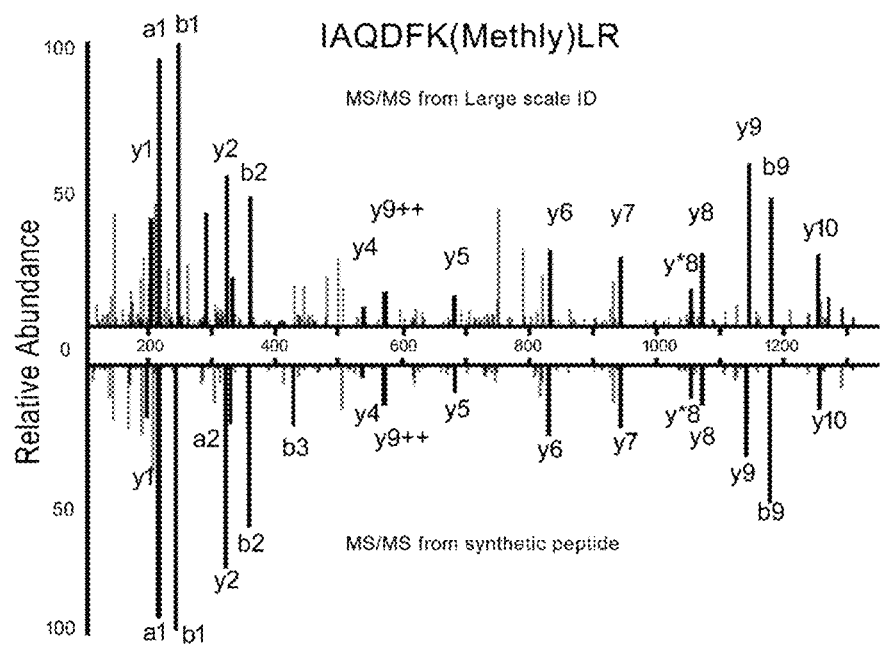
Figure 20D:
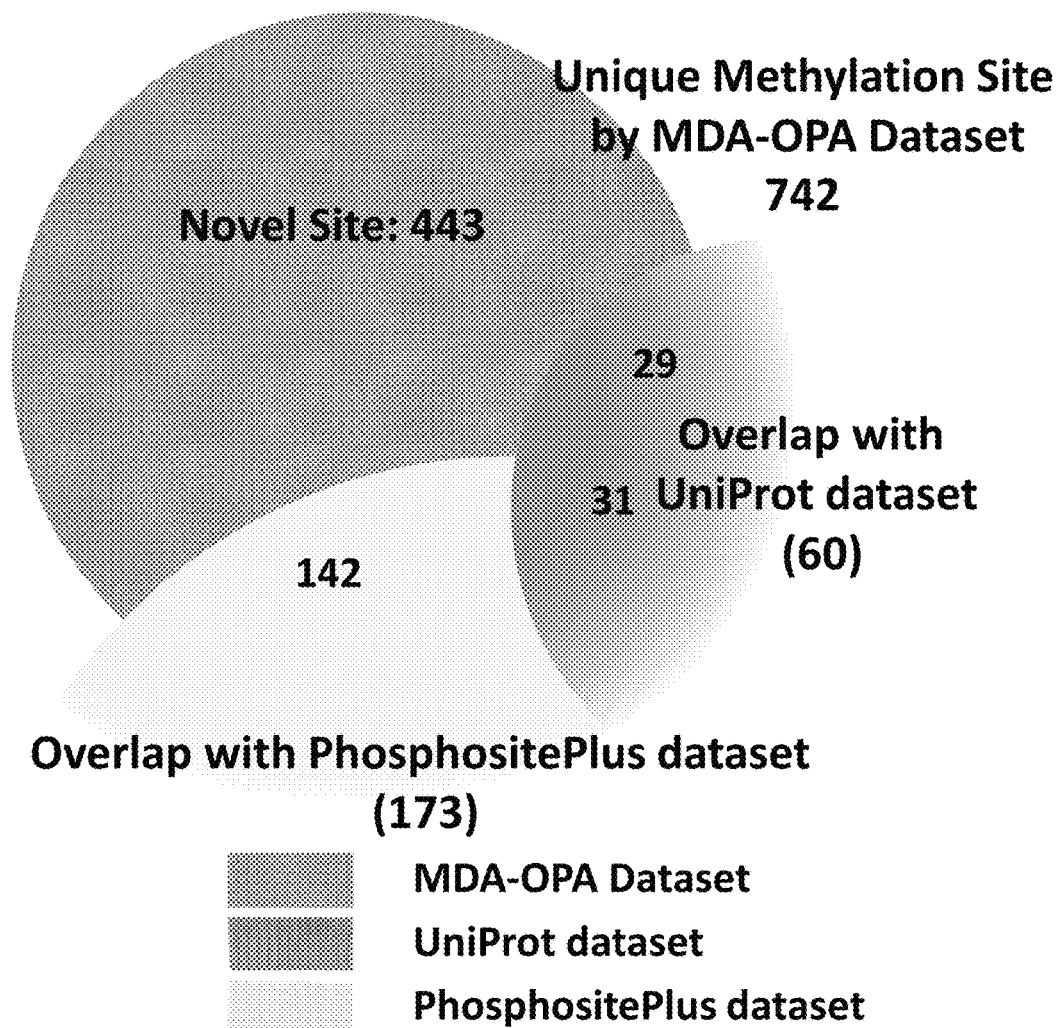

The threshold to consider peptide matches significant by Mascot database searches increased due to the multiple variable modification (FIG. 1D; David N. Perkins, D.J.C.P.D.M.C.J.S.C., Electrophoresis 20: 3551-3567 (1999)). Mass spectrometry raw data and associated peptide identification details are available under accession numbers PXD001599, PXD001688, and PXD001689 in ProteomeXchange. Above these significant thresholds (Mascot score for mono-methylation: >34.2, di-methylation: >28.8, and tri-methylation: >31.2), the false positive rate introduced by the multi-variable for MDA or OPA modifications was negligible (lower than 0.0002%; see FIG. 1E). Five identified methylation sites were selected for validation and the corresponding methylated peptides were synthesized and subjected to the chemical reactions (FIGS. 11-15). The MS/MS spectra of four synthetic peptides matched the experimental results. Examples of peptide "IAQDFK(mono-Met)LR" are shown in FIGS. 1F and 20c. It is believed that PTM sites are generally on the protein surface, especially methylation and ester-linked phosphorylation, and several reports have observed methylation events on tryptic peptides with C-terminal lysines (trypsin is generally believed to cleave after methylated lysine or arginine residues, albeit with much lower efficiency), as reviewed by Pang, C. N. et al., J. Proteome Res. 6:1833-1845 (2007)). Although cleavage after mono- and dimethylated lysines is less efficient, these peptides can be enriched and identified by our negative-selection workflow. Protein surface accessibility analysis showed significant enrichment (p=6.3e-47) for methylated lysine and arginine residues on the surface of proteins (against all amino acids of methylated proteins as background). For example, novel methylation events in our dataset, e.g. tri-methylation of K122 of 14-3-3 protein sigma (P31947), mono-methylation on K139 and K212 of 14-3-3 protein theta (P27348), mono-methylation on K106, K186 and mono-/tri-methylation on K256 of triosephosphate isomerase (P60174) were all located on the surface of the proteins (FIGS. 10, 19, which represent results from two different experiments).

It is noted that, as C-terminal esterification was efficiently suppressed as discussed above, we decided to keep C-terminally mono- and dimethylated peptides in our dataset, our confidence being further strengthened by the presence of 21 peptides with C-terminal methylation events in the PhosphositePlus (Hornbeck, P. V. et al., Nucleic Acids Res. 43: D512-520, 2015) or UniProt protein methylation databases. Antibody- or domain-based enrichment strategies are less likely to identify such cleavage events as they require flanking sequences before and after the methylated lysine. Therefore, any identified peptide with C-terminal methylation should be discarded. We arbitrarily excluded all of the C-terminally trimethylated peptides, as we could not verify the efficacy of trypsin on trimethylated lysine, which is expected to be extremely slow. Five identified methylation events were selected for validation by synthesized peptide analysis, four of which were validated via the same workflow as described herein. Thus an example peptide, "IAQDFK(Methyl)LR", is shown in FIGS. 1F and 20c, with very similar fragment patterns and matches.

Databases of protein methylation events are limited compared to other PTM analysis such as protein phosphorylation. There was only 12.5% overlap between a recently reported antibody based approach for the identification of protein methylation and the Phosphositeplus database (version Sep. 5, 2014) (Guo, A. et al., Mol. Cell. Proteomics 13: 372-387 (2014)). In contrast, 28% of our 793 identified methylation sites were present in the PhosphositePlus and Uniprot methylation databases (FIG. 2a). Interestingly, most of the known histone methylation events were recapitulated in our workflow. Motif analysis of the flanking sequences surrounding the methylated amino acid (Beausoleil, S. A. et al., Nat. Biotechnol. 24: 1285-1292 (2006)) revealed a RGG-rich motif for arginine methylation consistent with the literature (FIGS. 2B, 2E) (Shi, S. P. et al., PloS one 7, e38772 (2012); Bremang, M. et al., Mol. Biosyst. 9: 2231-2247 (2013); Boisvert, F. M. et al., Mol. Cell. Proteomics 2: 1319-1330 (2003)). In contrast, lysine methylation did not show strong consensus sequence except for mono-methylation. The flanking sequence of this PTM showed a significant enrichment of lysine residues on the C-terminal side, while small hydrophobic amino acids and glycine residues were enriched on the N-terminus of mono-methyl lysine (FIG. 2B).

Figure 2D:
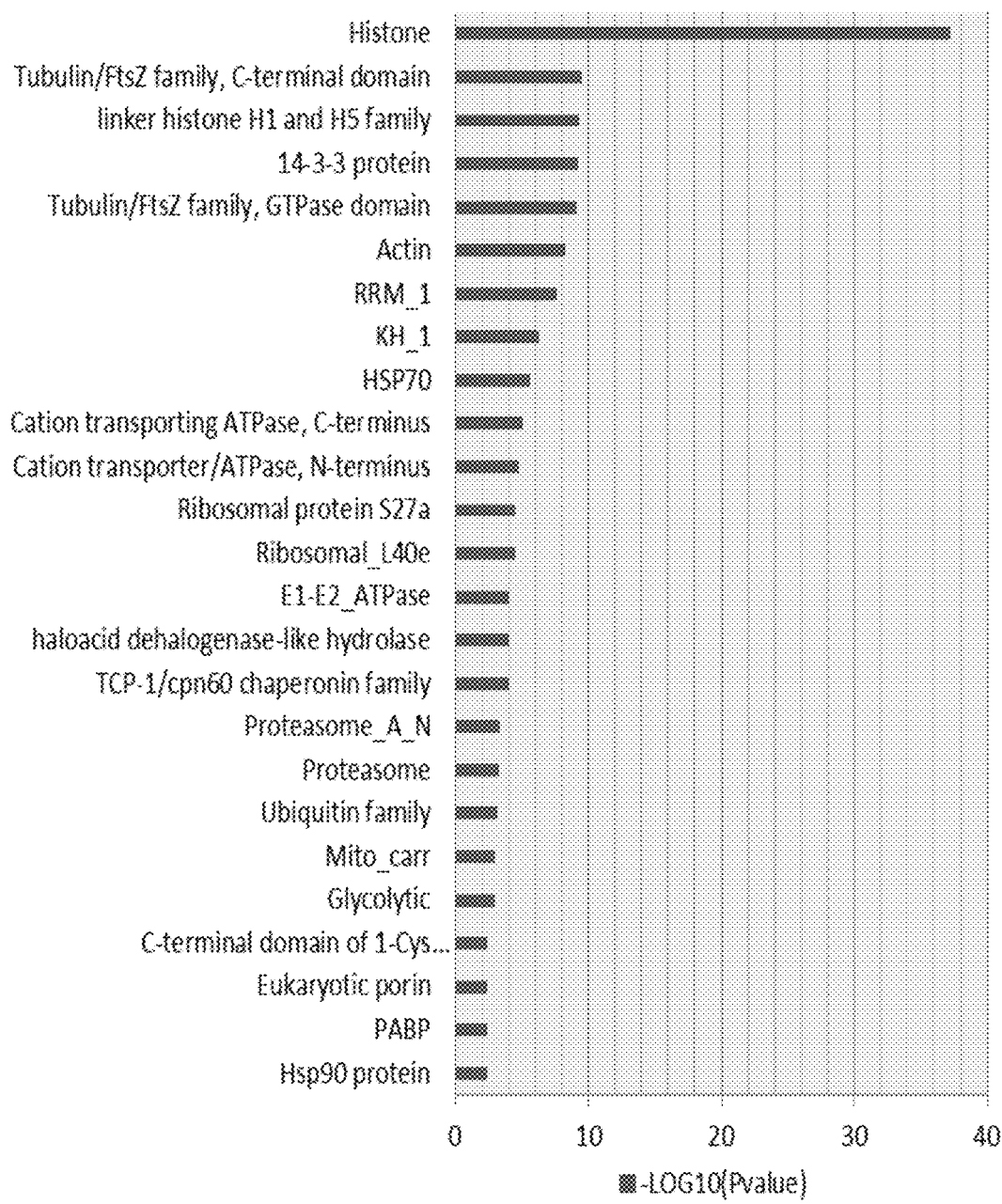

There are so far 11 proteins known with RGG-box in UniProt (October, 2013), three of which were found in this study (Q9NY12, Q32P51, P09651) with arginine methylation, and two (P61978, Q00839) with lysine methylation. Pfam protein domain analysis showed very consistent results with previous reports (Bremang, M. et al., Mol. Biosyst. 9: 2231-2247 (2013)), with significant enrichment of the RNA recognition motif (RRM_1) as shown in FIGS. 2C and 2D. Enrichment of proteins methylated on arginine residue that contain KH24, LSM, SAP, and Zn-finger domains was also observed (Bremang, M. et al., Mol. Biosyst. 9: 2231-2247 (2013)). Interestingly some cell structure proteins, such as actin and tubulin were also enriched in our dataset. Actin was found to be mono-, di- and tri-methylated on K63 in our data. These methylation sites have seldom been reported before (Li, M. M. et al., Nature communications 4: 1832 (2013)).

Estimation of FDR Introduced by the MDA OPA Modification.

MDA and OPA modification can introduce false positives in terms of methylation identification as the peptide mixture is more complex following the reactions. The increased complexity of the sample is not an issue when using high resolution/mass accuracy mass spectrometer such as an Orbitrap mass spectrometer (less than 10 ppm for both precursor and fragments). We tested whether the increased number of variable modifications affected the FDR. Briefly, protein extract from HEK 293 was processed using our workflow with the exceptions that no MDA-OPA reactions were performed. The MS results were searched with the same parameters which assumed that the chemical modifications are present. Any MSMS spectra matched to a peptide with MDA or OPA modification would therefore represent false positives as the peptides are not chemically modified. In this case, the FDR of MDA-OPA from this background search can be used to estimate the random FDR brought by multiple-variable-modification search for MDA-OPA reaction, as well as other modifications. The FDR estimated is shown in FIG. 1E.

Materials and Methods

Chemicals.

All standard proteins and chemicals (beta casein, myoglobulin, bovine albumin, alpha casein and lysozyme), 1,1,3,3-tetramethoxypropane, Amberlite IR-120 resin, urea, dithiothreitol (DTT), iodoacetamide (IAA), ammonium bicarbonate (ABC), formic acid (FA), isopropanol, citric acid, β-2-mercaptoethanol) were obtained from Sigma Aldrich (St. Louis, Mo., USA). Water and acetonitrile (ACN) for HPLC were obtained from JT Baker (Phillipsburg, N.J., USA). Trypsin was purchased from Worthington Biochemical Corp (Lakewood, N.J., USA). Bio-Rad protein assay kit II (500-0002) and DC protein assay kit II (500-0112) were from Bio-Rad (Mississauga, ON, Canada). All of the chemicals were of analytical purity grade except ACN and FA, which were of HPLC grade. All the water used in the experiment was prepared using a Milli-Q system (Millipore, Bedford, Mass., USA).

Sample Preparation.

Briefly, HeLa and HEK293 cells were grown to 80% confluence in 15 cm dishes and harvested in modified RIPA buffer (25 mM Tris-HCl (pH 7.6), 150 mM NaCl, 1% NP-40, 1% sodium deoxycholate, 0.5% SDS) after two washes with PBS. Sonication was applied for 1 min with 20 seconds pulse to increase protein extraction. Proteins were precipitated to remove detergent by adding 5× volume of cold acetone overnight followed by two washes with cold acetone. The protein pellet was then reconstituted in 8 M urea in 50 mM ammonium bicarbonate (ABC) and quantified by the DC protein assay kit (BioRad). Reduction and alkylation were done by adding dithiothreitol (DTT) to a final concentration of 10 mM at 56° C. for 30 min followed by 20 mM iodoacetamide (IAA) at room temperature. The solution was then diluted 5 times by adding 50 mM ABC. Trypsin was added to achieve a protein-enzyme ratio of 50:1. Digestion was performed at 37° C. overnight, with continuous head-to-end rotating. Digested peptides were then desalted on Sep-Pak $C_{18}$ SPE column (Waters, Mississauga, ON, Canada), aliquoted and dried down by SpeedVac (ThermoFisher Scientific, San Jose, Calif., USA).

For the conformation of the stable products from the OPA reactions, we used a tryptic digest of five standard proteins (beta casein, myoglobulin, bovine albumin, alpha casein and lysozyme). The digestion was done by standard protein in-solution digestion protocol as described above for cell lysate digestion. Bovine serum albumin (BSA) tryptic digest was prepared with the same protocol for the MDA derivatization and optimization.

BSA Methylation.

BSA for the methylation spike-in was prepared according to the protocols described previously (Kleifeld, O. et al., Nat. Biotechnol. 28: 281-288 (2010)). Briefly, 100 μg BSA protein was dissolved in 2M urea in 50 mM ABC, then reduced by 10 mM DTT at 56° C. for 30 min, then alkylated by 20 mM iodoacetamide for 45 min in the dark. Then the sample was labeled by addition of 20 mM formaldehyde and 10 mM $NaCNBH_3$ (Sigma Aldrich) for 16 hours. The labeling reaction was quenched by addition of 100 mM ABC. BSA protein was then precipitated, reconstituted in 1M urea and aliquoted into 1 μg for spike-in experiments, or digested overnight by trypsin (Worthington Biochemical). For bovine serum albumin (BSA) methylation spike-in experiments, HeLa lysate was digested along with methylated BSA.

Reagent Preparation.

Synthesis of 1,1,3,3-tetraisopropoxypropane (TiPP) was adapted from Foettinger et al. (Foettinger, A. et al., J. Mass. Spectrom. 41: 623-632 (2006)). Briefly, Amberlite IR-120 resin (5.5 g) (strong cation exchanger (SCX), HC-form, Sigma Aldrich) was thoroughly washed with isopropanol to remove the yellow color residue, and 4.95 ml (30 mmol) 1,1,3,3-tetramethoxypropane (Sigma Aldrich) dissolved in 182 ml (2.4 mol) isopropanol was added to the resin. The mixture was shaken for 2 hours. The solvent was decanted; the isopropanol and released methanol were then removed by rotary evaporation at 60° C. and the residue was re-dissolved in 182 mL isopropanol and again added to the SCX resin. This whole procedure (shaking, evaporating, re-dissolving) was repeated four times, and approximately 3.5 mL of pale yellow TiPP solution was obtained. The solution was aliquoted in amber tubes and stored at −80° C. before usage.

For the OPA reaction, 1 mL of 10× stock solution of OPA reaction buffer was prepared by adding 5 mg OPA (MW: 134.13) and 5 μL β2-mercaptoethanol (Density: 1.11 g/mL, MW: 78.13, molar ratio comes to about 2:1) into 100 μL pure ethanol, then diluted in 900 μL 50 mM carbonate buffer (pH 10.5). The stock solution was always freshly made in amber tube, and diluted 10 times by 50 mM carbonate buffer before usage in 2 hours.

MDA Derivatization and Optimization.

Twenty picomolar BSA trypsin digestion was used for each MDA derivatization optimization. Ten microgram Hela digest was used for real sample application. Peptide was incubated with TiPP and HCl at room temperature in dark for 1 hr, then diluted 20× before RP-SPE purification. For the esterification check experiment, 5 µl methanol or ethanol, 200 µl HCl, along with 5, 10, 50, 100, 200 µl acetic acid were tested.

OPA Product Confirmation.

One milligram of HeLa protein tryptic digest was reacted with the 1×OPA reaction buffer. The product was transferred onto 96-well plates with three replicates, along with 1×OPA reaction buffer and tryptic peptides of the same final concentration in bicarbonate buffer, which was used to make the OPA reaction buffer. The UV absorbance at 340 nm and the fluorescence at 455 nm were recorded over time to monitor the products up to 6 days. Tryptic digest from five standard proteins (as described above) was subjected to the OPA reaction, SCX purification to remove polymer and desalting. To confirm which OPA reaction products can be detected by mass spectrometry, two variable modifications representing the intermediate product (C(10)H(8)OS with MW of 176.0295845689, named as OPA-large) and the expected stable product (C(8)H(4)O with MW of 116.0262147505, named as OPA-small) were added as extra variable modification for database searching. The OPA reaction efficiency was tested on 10 µg HeLa digest, using the same protocol described above. The product was desalted and analyzed on an LTQ mass spectrometer.

Tandem Chemical Reaction and SCX Fractionation.

The core chemical modification of the workflow consists of two derivatization reactions on arginine and lysine residues sequentially. The malondialdehyde (MDA) reaction was from Foettinger et al. (Foettinger, A. et al., J. Mass. Spectrom. 41: 623-632 (2006)). Dried protein tryptic digest of 1 mg was mixed with 30 µL TiPP and 200 µL 12 M HCl, vortexed and kept in the dark for 1 hr to introduce the MDA modification on un-methylated arginine residues. The solution was then diluted 20 times, and loaded onto activated SCX SPE column (50 mg HyperSep™ SCX, Thermo Scientific, Waltham, Mass., USA). 80% ACN with 0.1% formic acid (FA) was used to wash the column to avoid polymer contamination. The column was then eluted by 2 mL 50 mM $Na_2CO_3$ and 2 mM 50 mM NaOH to recover the bound peptides. Then 450 µL of 10×OPA reaction buffer was added to the 4 mL SCX elution from the MDA reaction for OPA reaction. The reaction was kept in the dark and at room temperature for another 2 hours. After the OPA reaction, 5% of FA was used to lower the pH to 3. The solution was then loaded onto an activated SCX SPE column and washed by 80% ACN. Britton & Robinson buffers at different pH (20 mM $CH_3COOH$, 20 mM $H_3PO_4$, 20 mM$H_3BO_3$, adjusted to pH 6, 8, 10, 11, 12 by NaOH) were used to elute the peptides off the column sequentially. The eluent was desalted and dried down for MS analysis.

For MDA efficiency test, 10 µg of HeLa was reacted to 30 µL TiPP in 200 HCl. The product was SCX purified and desalted using the same procedure described above. For the OPA efficiency test, 5 µg of digest of the five standard proteins was treated with 1 mL 1×OPA reaction buffer for 2 hours. Both products were SCX purified to remove polymer contaminant and then desalted before MS analysis.

Tandem Chemical Reaction and SCX Fractionation on Large Scale Methylation Profiling.

The core chemical modification of the workflow consisted of two derivatization reactions on arginine and lysine residues sequentially. The malondialdehyde (MDA) reaction was adapted from Foettinger et al. (Foettinger, A. et al., J. Mass. Spectrom. 41: 623-632 (2006)). To exhaust any residual alcohol and provide excessive carboxyl group 70 µl acetic acid was mixed with 30 µL TiPP and 200 µL 12 M HCl for 10 min in room temperature. Five hundred microgram of Hela tryptic digest was mixed with the pre-mixed reaction buffer, vortexed and kept in dark for 1 hr to introduce the MDA modification on un-methylated arginine residues. The solution was then diluted 20 times, and loaded onto activated RP SPE column (50 mg SepPak™, Waters). The column was eluted by 80% ACN with 0.1% formic acid (FA). The eluent was then loaded onto SCX SPE column (50 mg HyperSep™ SCX, Thermo) to remove polymer side products. The SCX column was eluted by 2 mL 50 mM $Na_2CO_3$ and 2 mM 50 mM NaOH to recovery the bound peptides. Then 450 µL of 10×OPA reaction buffer was added to the 4 mL SCX elutiion for OPA reaction. The reaction was kept in dark and at room temperature for another 2 hours. After OPA reaction, 5% of FA was used to lower the pH to 3. The solution was then loaded onto an activated SCX SPE column and washed by 80% ACN. Britton & Robinson buffers at different pH (20 mM $CH_3COOH$, 20 mM $H_3PO_4$, 20 mM$H_3BO_3$, adjusted to pH 6, 8, 10, 11, 12 by NaOH) were used to elute the peptides off the column sequentially. The eluent was desalted and dried down for MS analysis. The OPA derivatization peptides was also desalted and loaded to online SCX fractionation coupled to MS analysis to minimize sample loss. The online SCX fractionation was achieved by step elution of up to 1M ammonium formate.

MS Analysis.

All the dried samples were reconstituted in 20 µL 0.5% FA and loaded at 4 µL for MS analysis. MS analysis platforms consisted of an Agilent 1100 capillary-HPLC system (Agilent Technologies, Santa Clara, Calif., USA) coupled with LTQ-Orbitrap or LTQ mass spectrometer (ThermoFisher Scientific, San Jose, Calif.), or Eksigent Nano-2D plus nano LC (AB Sciex, Framingham, Mass., USA) coupled to Q-Exactive (ThermoFisher Scientific, San Jose, Calif.). All systems were equipped with a nanoelectrospray interface operated in positive ion mode. The mobile phases consisted of 0.1% (v/v) FA in water as buffer A and 0.1% (v/v) FA in acetonitrile as buffer B. Peptide separation was performed on a 75 µm×150 mm analytical column packed in-house with reverse phase Magic C18AQ resins (1.9 µm; 100-Å pore size; Dr. Maisch GmbH, Ammerbuch, Germany). Briefly, 4 µL of sample was loaded onto the column using 98% buffer A at a flow rate of 300 nL/min for 20 min. Then, a gradient from 10% to 50% buffer was performed in 60 min, 120 min or 180 min at a flow rate of ~300 nL/min obtained from splitting a 20 µL/min through a restrictor or directly from the nano-HPLC. The MS method consisted of one full MS scan from 350 to 1,700 m/z followed by 5 data-dependent MS/MS CID scan of the most intense ions in ion trap on Orbitrap XL and LTQ, or 10 HCD MS2 scans on Q-Exactive. A dynamic exclusion repeat count of 2, and a repeat duration of 90 s were used. The resolution of full MS was set at 60,000 defined at m/z 400 on LTQ-Orbitrap or 7,500 defined at m/z 200 on Q-Exactive. To improve the mass accuracy, all the measurements in Orbitrap mass analyzer were performed with internal recalibration ("Lock Mass") at 445.1205.27. The charge state rejection function was enabled, with single and "unassigned" charge states rejected.

Database Search and Bioinformatics Analysis.

The database search was done either by Maxquant 1.3.0.5 (Cox, J. & Mann, M., Nat, Biotechnol, 26: 1367-1372 (2008)) or Mascot 2.3 (Perkins, D. N. et al., Electrophoresis 20: 3551-3567 (1999)). The raw files were searched against Uniprot protein fasta database (2013, July version), including commonly observed contaminants. For the OPA modification efficiency test, we used yeast database plus 5 standard proteins, named as YAL01SD to YAL05SD. Most of the parameters used for both search engines are the same: cysteine carbamidomethylation (+57.021463) was selected as fixed modification; variable modifications were set as follows: methionine oxidation, protein N-terminal acetylation, MDA modification on arginine residue, OPA modification on peptide N-terminal and lysine, mono- and di-methylation on both lysine and arginine residue, tri-methylation on lysine residue. The combination of methionine oxidation, protein N-terminal acetylation and MDA modification on arginine residue was set for the MDA reaction efficiency test, while methionine oxidation, protein N-terminal acetylation and OPA on modification on peptide N-terminal and lysine were set for OPA reaction efficiency test. Enzyme specificity was always set to trypsin. Up to two missing cleavages of trypsin were allowed. Precursor ion mass tolerances were 7 ppm, and fragment ion mass tolerance was 0.5 Da for CID MS/MS spectra, 20 ppm for HCD spectra for Maxquant, and 20 mmu for Mascot. The false discovery rate (FDR) for modified peptide, peptide and protein were all set at 1% and a minimum length of six amino acids was used for peptide filtration. The .dat files generated by Mascot were parsed and filtered by BuildSummary in Proteomics Tools (Sheng, Q. et al., Journal of Proteome Research 11: 1494-1502 (2012)), with a peptide FDR of 1%, then a home-written Perl script was used to do the FDR filtration on methylated peptides and unique peptide assignment. Symbols in the results for all variable modifications are illustrated in Table 1.

TABLE 1

Modifications and symbols for Mascot search result interpretation.

| index | Symbols | Modifications | Comment |
|---|---|---|---|
| 1 | * | Acetylation | delta1 = 42.010565, Acetyl (Protein N-term) |
| 2 | # | MDA | delta2 = 36.000000, MDA (R) |
| 3 | @ | Di-K/R | delta3 = 28.031300, Methyl-Di (KR) |
| 4 | & | Mono-K/R | delta4 = 14.015650, Methyl-Mono (KR) |
| 5 | ^ | Tri-K | delta5 = 42.046950, Methyl-Tri (K) |

TABLE 1-continued

Modifications and symbols for Mascot search result interpretation.

| index | Symbols | Modifications | Comment |
|---|---|---|---|
| 6 | % | OPA K | delta6 = 116.026215, OPA (K) |
| 7 | $ | OPA N-term | delta7 = 116.026215, OPA (N-term) |
| 8 | ~ | Oxidation | delta8 = 15.994915, Oxidation (M) |

Public dataset of methylation was downloaded from Uniprot and PhosphositsPlus (http://www.phosphosite.org/) (Hornbeck, P. V. et al., Nucleic Acids Res. 40: D261-270 (2012)). Pfam protein domain analysis was done by DAVID (http://david.abcc.ncifcrf.gov/) (Huang da, W. et al., Nature protocols 4: 44-57 (2009)). Consensus sequence analysis was performed with the iceLogo web tool (http://iomics.u-gent.be/icelogoserver/main.html) using standard settings (Colaert, N. et al., Nat. Methods 6: 786-787 (2009)). Motif-X analysis was done using the online tool with default filtering criteria (http://motif-x.med.harvard.edu/). Protein methylation modeling was displayed by PyMOL.

NetSurfP (Petersen, B. et al., BMC Struct Biol. 9: 51 (2009)) was used to calculate the surface accessibility of all the amino acids for identified proteins, defined as buried or exposed. The enrichment of the methylated amino acid was assessed by the hypergeometric p-values by "phyper" in R (https://www.r-project.org/). Public dataset of methylation was downloaded from Uniprot and PhosphositsPlus ENREF 9 (P. V. Hornbeck, P. V. et al., Nucleic Acids Res. 40: D261-270 (2012)). UniProt methylation list was extracted from downloaded gff format human database. The unique methylation site was assigned back to all possible proteins, then compared with the format reorganized PhosphositePlus database (only site with definite sites localization information were used) and UniProt database.

To test how much the increased number of variable modifications affected the FDR for methylation identification, protein extract from HEK 293 was processed using our workflow with the exceptions that no MDA-OPA reactions were performed. The MS results were searched with the same parameters which assumed that the chemical modifications are present. Any MS spectra matched to a peptide with MDA or OPA modification would therefore represent false positives as the peptides are not chemically modified. In this case, the FDR of MDA-OPA from this background search can be used to estimate the random FDR brought by multiple-variable-modification search for MDA-OPA reaction, as well as other modifications.

Information of synthesized peptide identification. This information is given in Table 2 and in FIGS. 11-15.

TABLE 2

Synthesized peptide identification.

| ID | Peptide | Comment | Validated? | Identified Sequence |
|---|---|---|---|---|
| 1 | EIAQDFK(mono-meth)TDLR | MONO-methyl on K | yes | R.$EIAQDFK&TDLR#.F |
| 2 | EIAQDFK(tri-meth)TDLR | tri-methyl on K | yes | R.$EIAQDFK^TDLR#.F |
| 3 | QYK(Di-meth)GiiDCVVR | DI-methyl on K | No | K.$QYK@GIIDCVVR#.I |
| 4 | QYK(tri-meth)GiiDCVVR | tri-methyl on K | yes | K.$QYK^GIIDCVVR#.I |
| 5 | MDSTEPPYSQK(Di-meth)R | DI-methyl on k | yes | K.$MDSTEPPYSQK@R#.Y |

In summary, we have described the first chemistry-based strategy for the high-throughput discovery of lysine and arginine methylation events. The approach may have one or more of the following advantages: be simple; be inexpensive; and/or does not rely on specific antibodies to perform charge-based methylated peptide enrichment and identification by MS. This methodology may also be generic and non-sequence-biased, having the potential to be used for large-scale methylome profiling and methyltransferase/demethylase discovery, which can have application in several important areas such as cancer research.

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

The contents of all documents and references cited herein are hereby incorporated by reference in their entirety.

What is claimed is:

1. A method for identifying methylation on arginine and lysine residues in a set of peptides, the method comprising: i) obtaining the set of peptides; ii) blocking un-methylated arginine and lysine residues and the free N-terminal amine of peptides in the set of peptides, so that un-methylated peptides are neutralized and only methylated peptides are positively charged at neutral or basic pH; iii) isolating methylated peptides based on charge; and iv) performing mass spectrometry (MS) analysis on the isolated methylated peptides to detect methylated lysine and arginine residues.

2. The method of claim 1, wherein step (ii) comprises converting the guanidine group on un-methylated arginine residues to a 2-pyrimidine residue.

3. The method of claim 2, wherein said conversion of the guanidine group comprises reacting with malondialdehyde (MDA) or an acetal or derivative thereof, or reaction with 1,1,3,3-tetraisopropoxypropane (TiPP).

4. The method of claim 1, wherein step (ii) comprises blocking the epsilon primary amine on un-methylated lysine residues and blocking the free primary amine on the peptide N-terminals; or step (ii) comprises blocking un-methylated arginine and lysine residues regardless of peptide sequence.

5. The method of claim 4, wherein said blocking comprises reaction with ortho-phthalaldehyde (OPA) or a derivative thereof.

6. The method of claim 1, wherein step (ii) comprises sequentially reacting with MDA or TiPP, followed by reacting with OPA.

7. The method of claim 1, wherein step (iii) comprises ion exchange fractionation.

8. The method of claim 7, wherein said ion exchange fractionation comprises strong cation exchange (SCX) or solid phase extraction (SPE).

9. The method of claim 1, wherein said set of peptides comprises tryptic peptides obtained by digesting a set of proteins with trypsin.

10. The method of claim 9, wherein said set of proteins is present in a cellular extract or lysate.

11. A method for large scale profiling of protein methylation in a cell or tissue, the method comprising: i) digesting proteins from the cell or tissue with trypsin, to provide a set of tryptic peptides; ii) blocking un-methylated arginine and lysine residues and the free N-terminal amine of peptides in the tryptic set of peptides, so that un-methylated peptides are neutralized and only methylated peptides are positively charged at neutral or basic pH; iii) isolating methylated peptides based on charge; and iv) performing mass spectrometry (MS) analysis on the isolated methylated peptides to detect methylated lysine and arginine residues.

12. The method of claim 11, wherein: step (ii) comprises conversion of the guanidine group on un-methylated arginine residues to a 2-pyrimidine residue, said conversion of the guanidine group comprising reaction with malondialdehyde (MDA) or reaction with 1,1,3,3-tetraisopropoxypropane (TiPP); or step (ii) comprises blocking the epsilon primary amine on un-methylated lysine residues and blocking the free primary amine on the peptide N-terminals; or step (ii) comprises blocking un-methylated arginine and lysine residues regardless of peptide sequence.

13. The method of claim 11, wherein said blocking comprises reaction with ortho-phthalaldehyde (OPA).

14. The method of claim 11, wherein step (ii) comprises sequentially reacting with MDA or TiPP, followed by reacting with OPA.

15. The method of claim 11, wherein step (iii) comprises ion exchange fractionation.

16. The method of claim 15, wherein said ion exchange fractionation comprises strong cation exchange (SCX) or solid phase extraction (SPE).

17. The method of claim 1 wherein said conversion of the guanidine group comprises reaction with 1,1,3,3-tetraisopropoxypropane (TiPP) in an acidic aqueous environment, optionally in the presence of hydrochloric acid (HCl), optionally wherein said TiPP and HCl are pre-incubated with an excess of acetic acid before reaction with the un-methylated peptides such that protein esterification is suppressed.

\* \* \* \* \*